(12) United States Patent
Keily et al.

(10) Patent No.: US 11,369,710 B2
(45) Date of Patent: Jun. 28, 2022

(54) FRAGRANCE DISPENSERS AND METHODS

(71) Applicant: Dispensing Dynamics International, Inc., San Marcos, CA (US)

(72) Inventors: Joel P. Keily, City of Industry, CA (US); Victor Landa, City of Industry, CA (US)

(73) Assignee: Dispensing Dynamics International, Inc., San Marcos, CA (US)

( * ) Notice: Subject to any disclaimer, the term of this patent is extended or adjusted under 35 U.S.C. 154(b) by 187 days.

(21) Appl. No.: 16/874,519

(22) Filed: May 14, 2020

(65) Prior Publication Data
US 2020/0360558 A1 Nov. 19, 2020

Related U.S. Application Data

(60) Provisional application No. 62/849,082, filed on May 16, 2019, provisional application No. 62/913,996, filed on Oct. 11, 2019, provisional application No. 63/011,792, filed on Apr. 17, 2020.

(51) Int. Cl.
*A61L 9/12* (2006.01)
(52) U.S. Cl.
CPC .......... *A61L 9/122* (2013.01); *A61L 2209/111* (2013.01); *A61L 2209/133* (2013.01); *A61L 2209/15* (2013.01)
(58) Field of Classification Search
None
See application file for complete search history.

(56) References Cited

U.S. PATENT DOCUMENTS

| | | | |
|---|---|---|---|
| 1,929,334 A | 10/1933 | Sabatine |
| 3,150,800 A | 9/1964 | Weber, III |
| 3,211,336 A | 10/1965 | Gasser |
| 3,214,062 A | 10/1965 | Mahon |
| 3,358,885 A | 12/1967 | Flowers |
| 3,659,791 A | 5/1972 | Clark |

(Continued)

FOREIGN PATENT DOCUMENTS

| | | |
|---|---|---|
| DE | 94 02 313 U1 | 3/1994 |
| EP | 0365770 A1 | 5/1990 |

(Continued)

OTHER PUBLICATIONS

"Lanzamiento mundial de última tecnología: AromaNebulyser", Marketing Olfativo, 2011, with partial English translation in 9 pages, archived at https://web.archive.org/web/20111113054246/https://www.aromarketing.es/noticias.

(Continued)

*Primary Examiner* — Jelitza M Perez
(74) *Attorney, Agent, or Firm* — Knobbe, Martens, Olson & Bear, LLP

(57) ABSTRACT

Various fragrance dispensers are disclosed. The fragrance dispenser can include a core unit that has a connection unit and a control unit. The fragrance dispenser can include a cartridge that is configured to engage with the core unit. The cartridge can include an impeller and a fragrant material. The fragrance dispenser can have a motor that drives the impeller, thereby dispersing the fragrance. The cartridge can be configured to disengage from the connection unit, such as when the cartridge reaches a depleted state.

25 Claims, 25 Drawing Sheets

(56) References Cited

U.S. PATENT DOCUMENTS

| | | | |
|---|---|---|---|
| 3,889,852 | A | 6/1975 | Strefford |
| 4,040,543 | A | 8/1977 | Guillen |
| 4,098,436 | A | 7/1978 | Kohlbeck |
| 4,111,338 | A | 9/1978 | Cheng et al. |
| 4,166,087 | A | 8/1979 | Cline et al. |
| 4,171,776 | A | 10/1979 | Pagliaro |
| 4,383,951 | A | 5/1983 | Palson |
| 4,579,258 | A | 4/1986 | Brown et al. |
| 4,615,476 | A | 10/1986 | Hobbs et al. |
| 4,789,083 | A | 12/1988 | Gutierrez |
| 4,931,258 | A | 6/1990 | Zlotnik et al. |
| 5,025,962 | A | 6/1991 | Renfro |
| 5,114,625 | A | 5/1992 | Gibson |
| 5,193,557 | A | 3/1993 | Hogan |
| 5,223,182 | A | 6/1993 | Steiner et al. |
| 5,249,718 | A | 10/1993 | Muderlak et al. |
| 5,449,117 | A | 9/1995 | Muderlak et al. |
| 5,480,591 | A | 1/1996 | Lagneaux et al. |
| 5,673,825 | A | 10/1997 | Chen |
| 5,713,492 | A | 2/1998 | DeGennaro |
| 5,823,390 | A | 10/1998 | Muderlak et al. |
| 5,884,808 | A | 3/1999 | Muderlak et al. |
| 5,904,273 | A | 5/1999 | Aspacher et al. |
| 6,039,212 | A | 3/2000 | Singh |
| 6,216,925 | B1 | 4/2001 | Garon |
| 6,318,600 | B1 | 11/2001 | Winnett et al. |
| 6,450,419 | B1 | 9/2002 | Martens, III et al. |
| 6,540,155 | B1 | 4/2003 | Yahav |
| 6,868,989 | B2 | 3/2005 | Fahy |
| 6,929,154 | B2 | 8/2005 | Grey et al. |
| 6,931,202 | B2 * | 8/2005 | Pedrotti .............. A01M 1/2077 392/395 |
| 7,157,057 | B2 | 1/2007 | Gohil |
| 7,244,398 | B2 | 7/2007 | Kotary et al. |
| 7,246,724 | B2 | 7/2007 | Dave |
| 7,299,951 | B2 | 11/2007 | Jahnke et al. |
| 7,631,783 | B1 | 12/2009 | Laible |
| 7,815,074 | B2 | 10/2010 | Ciavarella et al. |
| 7,854,354 | B2 | 12/2010 | Laible |
| 7,922,104 | B2 | 4/2011 | Zlotnik et al. |
| 8,157,188 | B2 | 4/2012 | Duston et al. |
| 8,573,447 | B2 | 11/2013 | Muderlak et al. |
| 8,860,347 | B2 | 10/2014 | Keily et al. |
| 8,889,082 | B2 | 11/2014 | Muderlak et al. |
| 8,931,713 | B2 | 1/2015 | Muderlak et al. |
| 9,156,603 | B1 | 10/2015 | Muderlak et al. |
| 2004/0265189 | A1 | 12/2004 | Schwartz |
| 2006/0163376 | A1 | 7/2006 | Lakatos et al. |
| 2006/0180143 | A1 | 8/2006 | Lind et al. |
| 2006/0222347 | A1 | 10/2006 | Wefler |
| 2006/0249593 | A1 | 11/2006 | Brown et al. |
| 2006/0261179 | A1 | 11/2006 | Davies et al. |
| 2007/0036673 | A1 | 2/2007 | Selander |
| 2007/0235555 | A1 | 10/2007 | Helf et al. |
| 2007/0290064 | A1 | 12/2007 | Majerowski et al. |
| 2008/0292508 | A1 | 11/2008 | Zlotnik et al. |
| 2009/0117012 | A1 | 5/2009 | Bankers et al. |
| 2009/0151061 | A1 | 6/2009 | Chen |
| 2009/0224064 | A1 | 9/2009 | Brodbeck et al. |
| 2010/0025427 | A1 | 2/2010 | Chiou et al. |
| 2010/0147972 | A1 | 6/2010 | Lakatos et al. |
| 2010/0196195 | A1 | 8/2010 | Moschel |
| 2012/0024975 | A1 | 2/2012 | Sharma et al. |
| 2013/0034444 | A1 | 2/2013 | Muderlak et al. |
| 2014/0115766 | A1 | 5/2014 | Muderlak et al. |

FOREIGN PATENT DOCUMENTS

| | | |
|---|---|---|
| EP | 1188451 A1 | 3/2002 |
| EP | 1352562 A1 | 10/2003 |
| EP | 2564878 A1 | 3/2013 |
| GB | 2392438 A | 3/2004 |
| GB | 2392439 A | 3/2004 |
| GB | 2392440 A | 3/2004 |
| GB | 2560571 A | 9/2018 |
| JP | 2003-012062 A | 1/2003 |
| WO | WO 95/09806 A1 | 4/1995 |
| WO | WO 2008/112545 A1 | 9/2008 |
| WO | WO 2012/125205 A1 | 9/2012 |
| WO | WO 2012/175972 A1 | 12/2012 |
| WO | WO 2013/066636 A1 | 5/2013 |
| WO | WO 2014/145372 A1 | 9/2014 |
| WO | WO 2017/053553 A1 | 3/2017 |

OTHER PUBLICATIONS

"Spraying Systems Spain, S.L (Autojet)—Pulverizadores de preenvasado", Interempresas, 2009, accessed Oct. 23, 2020, with English translation in 8 pages. URL: https://www.interempresas.net/Alimentaria/FeriaVirtual/Producto-Equipo-depulverizacion-de-aromas-y-conservantes-43373.html.
Print-out of page from website of Eachome Houseware (HK) Co., Ltd., accessed Oct. 22, 2020, in 1 page, archived at https://web.archive.org/web/20201023214242/https://hkeachome.weebly.com/.
International Search Report and Written Opinion, re PCT Application No. PCT/US2014/030123 dated Jul. 7, 2014.
International Preliminary Report on Patentability, re PCT Application No. PCT/US2014/030123 dated Sep. 24, 2015.
International Search Report and Written Opinion, re PCT Application No. PCT/US2020/032958 dated Sep. 7, 2020.
International Search Report and Written Opinion, re PCT Application No. PCT/US2012/000127 dated Aug. 23, 2012.
International Preliminary Report on Patentability, re PCT Application No. PCT/US2012/000127 dated Sep. 26, 2013.
International Search Report and Written Opinion, re PCT Application No. PCT/US2012/060943 dated Jan. 9, 2013.
International Preliminary Report on Patentability, re PCT Application No. PCT/US2012/060943 dated May 15, 2014.
International Partial Search Report, re PCT Application No. PCT/US2013/067131 dated Feb. 25, 2014.
International Preliminary Report on Patentability for PCT Application No. PCT/US2020/032958, dated Nov. 25, 2021.

\* cited by examiner

FRAGRANCE DISPENSERS AND METHODS

CROSS REFERENCE

This application claims the priority benefit of U.S. Provisional Patent Application No. 62/849,082, filed May 16, 2019, U.S. Provisional Patent Application No. 62/913,996, filed Oct. 11, 2019, and U.S. Provisional Patent Application No. 63/011,792, filed Apr. 17, 2020, the entirety of each of which is incorporated by reference herein.

BACKGROUND

Field

This disclosure generally relates to fragrance dispensers, such as automated dispensers with replaceable fragrance cartridges that are configured to indicate when replacement is due.

Description of Certain Related Art

Containers of fragrance, such as aerosol cans, can be used to deliver a pleasing scent to a space. The containers can be contained in a housing. Timers and other controls can be employed to control dispensation of the fragrance.

Overview of Certain Features

The fragrance dispenser can include a reservoir with the fragrant material. Some reservoirs comprise a fragrant liquid, such as an oil. However, liquid reservoirs can be messy and prone to spills. Some reservoirs are solid or gelatinous. For example, the fragrance can be contained in a substantially solid (e.g., gummy) substrate. A substantially solid reservoir can be convenient to store, handle, and use.

The reservoir may eventually become depleted, such as the fragrance becoming substantially exhausted and/or less potent. Some dispensers house the reservoir in a replaceable cartridge, which can make exchanging an exhausted reservoir with a fresh (e.g., non-exhausted) reservoir quick and easy.

However, it can be inconvenient to determine when and whether it is time to replace a cartridge. For example, a maintenance person may need to be physically present at the fragrance dispenser, open a door on the fragrance dispenser, and look inside to determine the status of the cartridge. This can be time consuming and inconvenient, especially if a facility has multiple fragrance dispensers. The extra steps needed to check the status of the cartridge may lead to maintenance personnel delaying such work, or not performing it at all. Thus, dispensers due for a fresh cartridge may go unmaintained.

It would be helpful to be able to tell from a remote position whether a cartridge in a dispenser is due for replacement. For example, it would be helpful to be able to tell from a visual inspection of the outside of the fragrance dispenser whether the cartridge is ready for replacement. This would allow, for example, a maintenance person to remotely scan (e.g., by sight) the fragrance dispenser, immediately know the status of the dispenser (e.g., whether the cartridge is exhausted), and/or make a disposition as to the dispenser (e.g., whether to replace the cartridge). The scan can be performed without having to open a door of the dispenser.

During use, air can enter the cartridge, pick up some of the fragrance, and exit the cartridge, thereby moving the fragrance into the space. To facilitate such movement, it can be desirable to actively, rather than passively, move the air. For example, it can be beneficial to have an airflow-enhancing element, such as one or more fan blades, that encourages air to flow over the fragrance reservoir. To reduce the number of components and/or to facilitate efficient dispensation of the fragrance, it can be helpful to have the blades themselves include the fragrance. For example, it can be advantageous to have the blades made of reservoir material and/or be part of the reservoir. The blades can be included in the replaceable cartridge.

A fragrance in the environment within the space may dissipate over time. Thus, additional dispensations of the fragrance may be needed. It can be desirable for a fragrance dispenser to control such dispensation to maintain a desired level of the fragrance in a space.

The various fragrance dispensers disclosed herein address one or more of the aforementioned concerns, or others.

According to some embodiments, a fragrance dispenser system comprises a housing. The housing can comprise a rigid material that is configured to house and/or protect other system components. The housing can have an opening on the bottom.

The fragrance dispenser system can include a core unit. The core unit can be located in the housing. The core unit can include a connection unit. The connection unit can include a securing element. The securing element can include one or more first positioning features (e.g., slots) and/or one or more first securing features (e.g., hooks). The connection unit can include an engagement element. The engagement element can include, for example, an annular member. The engagement element can be configured to move relative to the securing element and/or the housing. The connection unit can include a biasing member that biases the engagement element away from the securing element.

The fragrance dispenser system can include a control unit. The control unit can include a controller. The control unit can include a cartridge sensor, such as a switch. Some or all of the control unit can be located in the housing or outside of the housing (e.g., in a remote location). The control unit can be configured to govern the operation of other system components. For example, the control unit can control operation of a motor of the fragrance dispenser system. The motor can be an electric motor. The motor can have a drive shaft. The motor can be configured to rotate the drive shaft in a first rotational direction and a second rotational direction.

The fragrance dispenser system can include a cartridge. The cartridge can be configured to removably engage with the core unit, such as with the connection unit. The cartridge can include a casing. The casing can have one or more second positioning elements (e.g., posts). The second positioning element can be configured to mate with the first positioning element. The casing can include one or more second securing features (e.g., openings). The second securing feature can be configured to mate with the first securing feature. The cartridge can include an airflow element, such as an impeller. The cartridge can include a fragrant material, such as fragrant oil. The fragrant material can be embedded in the impeller.

The fragrance dispenser can be configured such that, when the cartridge is engaged with the core unit and the drive shaft spins in the first rotational direction, the impeller spins. This can distribute fragrance into the room or other space in which the dispenser is located.

The fragrance dispenser can be configured such that, when the drive shaft spins in the second rotational direction, the cartridge disengages from the connection unit. This can result in the cartridge separating from some or all of the core unit, such as from the securing element. In certain implementations, when the cartridge disengages from the connection unit, the cartridge falls downward (e.g., due to the force of gravity and/or the biasing member) and/or a bottom of the cartridge protrudes out of the bottom opening in the housing.

In some embodiments, the connection unit includes a control gear. The control gear can be movable by the motor. The control gear can be configured to engage with at least one of the second positioning features.

In several implementations, the connection unit has a one-way torque transmission device, such as a one-way bearing. The one-way torque transmission device can be configured to activate to transmit torque only when the drive shaft spins in one rotational direction, such as the second rotational direction.

In certain variants, the cartridge sensor is configured to detect that the cartridge is secured to the connection unit. The cartridge sensor can provide a signal to the controller, which can provide an indication to the user. For example, in response to the cartridge being secured to the connection unit, a light can be illuminated or change status (e.g., color).

Certain implementations of a fragrance dispenser system include a core unit that includes a connection unit, a control unit, and a motor. In some embodiments, the motor is part of the connection unit or the control unit. In certain variants, the fragrance dispenser system includes a housing, such as a hard plastic enclosure.

The fragrance dispenser system can include a cartridge. The cartridge can be configured to removably engage with the core unit. The cartridge can include an impeller and a fragrant material. In some implementations, the impeller comprises a lattice of thermoplastic elastomer.

The fragrance dispenser system can be configured such that the impeller is rotatable by the motor. In some variants, the control unit can determine that the cartridge has reached a depleted state, such as based on time. In response, the cartridge can be disengaged from the connection unit. This can result in, for example, the cartridge moving (e.g., dropping) from an engaged position to a disengaged position. In certain variants, the cartridge is retained in the disengaged position by a catch (e.g., a radially inward protrusion) on the housing.

According to some embodiments, the fragrance dispenser system includes a cartridge present sensor. The cartridge present sensor can be configured to detect that the cartridge is engaged with the connection unit. The cartridge present sensor can be, for example, a switch or proximity sensor. The cartridge present sensor can provide a signal to the controller, which can provide an indication to the user. For example, in response to detecting that the cartridge is engaged with the connection unit, a light can be illuminated or change status (e.g., color).

In certain embodiments, the fragrance dispenser system includes a cartridge secured sensor. The cartridge secured sensor can be configured to detect that the cartridge is secured to the connection unit. The cartridge present sensor can be, for example, a switch or proximity sensor. The cartridge secured sensor can provide a signal to the controller, which can provide an indication to the user. For example, in response to detecting that the cartridge is secured to the connection unit, a light can be illuminated or change status (e.g., color).

According to certain implementations, the connection unit has a support element and an engagement element. The support element can be configured to removably secure with the cartridge. The engagement element can be configured to move (e.g., slide) relative to the support element, such as in a generally vertical direction. A biasing member can bias the engagement element away from the support element.

The connection unit can have a torque-transmission element, such as a shaft, spline, gearing, or otherwise. The torque-transmission element can be configured to transfer torque from the motor to the impeller. The torque-transmission element can engage with a corresponding feature on the impeller. For example, a shaft of the connection unit can be received in a cavity of the impeller. In some implementations, the torque-transmission element and the impeller are configured to magnetically couple. For example, the shaft can include a magnet and the impeller can include a corresponding metallic component, such as a metal washer. In some implementations, when the cartridge is engaged with the core unit, the impeller is suspended above a stop on a bottom of the cartridge (e.g., by the force of the magnet). In some variants, the shaft has one or more radially outwardly extending wings.

A method of operating a fragrance dispenser can include receiving a fragrance cartridge into a housing of the fragrance dispenser. The method can include rotating the cartridge relative to a support element of the fragrance dispenser. In some embodiments, this causes engagement of the first and second securing features of the support element and cartridge, respectively. For example, a hook of the support element can be rotated relative to an opening in the cartridge.

The method can include operably connecting a motor of the fragrance dispenser with an airflow element, such as an impeller, of the fragrance cartridge. For example, a shaft of the support element can be engaged with (e.g., received into) a cavity of the impeller. The method can include spinning the impeller, such as by driving the motor in a first rotational direction.

The method can include disengaging (e.g., partially or completely ejecting) the cartridge. In certain implementations, the method includes driving the motor in a second rotational direction. In some variants, driving the motor in a second rotational direction can cause activation of a one-way torque transmission device. The method can include transmitting torque from the motor and via the one-way torque transmission device to the cartridge. In certain implementations, this can result in the cartridge rotating relative to the support element. The method can include disengaging the first and second securing features. The method can include releasing (e.g., dropping) the fragrance cartridge into a disengaged position. The method can include pushing the fragrance cartridge away from the support element with a biasing member. The method can include determining that the cartridge has reached a depleted state.

For purposes of summarizing the disclosure, certain aspects, advantages, and features of the technology have been described herein. Not necessarily any or all such advantages are achieved in accordance with any particular embodiment of the technology disclosed herein. No aspects of this disclosure are essential or indispensable. Neither the preceding summary nor the following detailed description purports to limit or define the scope of protection. The scope of protection is defined by the claims.

BRIEF DESCRIPTION OF THE DRAWINGS

Certain features of this disclosure are described below with reference to the drawings. The illustrated embodiments are intended to illustrate, but not to limit the embodiments. Various features of the different disclosed embodiments can be combined to form further embodiments, which are part of this disclosure.

DETAILED DESCRIPTION OF CERTAIN EMBODIMENTS

Various fragrance dispensers and related methods are described. Certain embodiments of the fragrance dispensers are described in the context of a fragrance dispenser with a replaceable cartridge having fragrant material in a substantially solid form and/or embedded in a substantially solid substrate, due to particular utility in that context. However, the embodiments and inventions disclosed herein can also be applied to other types of dispensers and other types of dispensed materials, such as fragrance dispensers that include fragrant material in a liquid, gel, or gaseous form, dispensers with non-replaceable cartridges, non-fragrance dispensers (e.g., humidifiers), or otherwise. No features, structure, or step disclosed herein is essential or indispensable.

I. Overview

Figure 1:
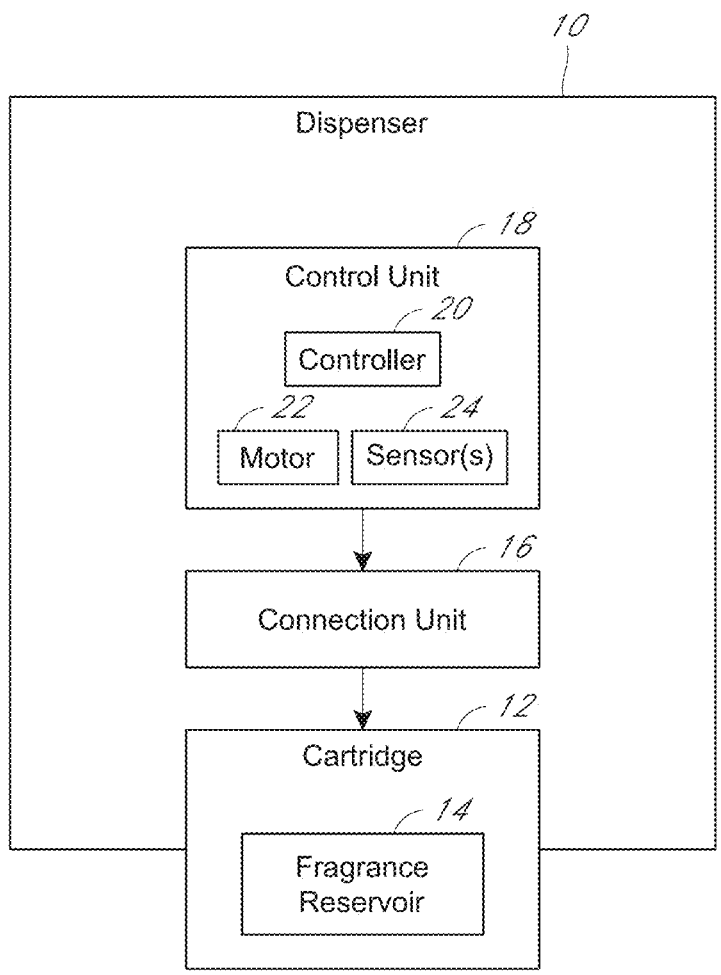
FIG. 1 schematically illustrates a fragrance dispenser.

FIG. 1 schematically illustrates a fragrance dispenser 10 (also called a dispenser). The dispenser 10 can be configured to dispense fragrance into a space in which the dispenser 10 is located, such as a bathroom, kitchen, or otherwise.

The dispenser 10 can include housing that receives a replaceable fragrance unit 12 (also called a refill or a cartridge) that includes the fragrance reservoir 14. The fragrance unit 12 can comprise a material that is odorizing or deodorizing. In some embodiments, the fragrance is embedded in a substrate, such as a polymer, carbohydrate (e.g., polysaccharide) or otherwise. The fragrance reservoir 14 can be substantially solid, such as being a highly viscous gel. The fragrance reservoir 14 can be solid enough to hold a shape. The fragrance reservoir 14 can be shaped as an impeller or other airflow-enhancing shape. The fragrance unit 12 can be positioned in an outer casing, which can protect the reservoir 14 and/or reduce the chance of a user touching the reservoir 14. The fragrance unit 12 can be removable from the rest of the dispenser, such as when the fragrant material has become exhausted, thereby allowing a new fragrance unit 12 to be installed in the dispenser 10.

The dispenser 10 can include a connection unit 16 that is configured to connect with the fragrance unit 12. In some embodiments, the connection unit 16 is configured to removably couple with the fragrance unit 12. For example, the connection unit 16 can comprise a bayonet mount. The connection unit 16 can be configured to automatically release (e.g., partially or completely eject) the fragrance unit 12, such as when the fragrance unit 12 is due for replacement.

The dispenser 10 can include a control unit 18 that directs certain operations of the dispenser 10. For example, the control unit 18 can be configured to control dispensation of the fragrance from the reservoir 14 and/or release of the fragrance unit 12 from the connection unit 16. The control unit 18 can include a controller 20, such as an electronic microprocessor and a memory. The control unit 18 can include a motor 22, such as an AC or DC electric motor, which can be controlled by the controller 20. The motor 22 can be configured to spin a fan, such as an impeller. The motor 22 can be configured to release the fragrance unit 12 from the connection unit 16, such as by rotating the fragrance unit 12 relative to the connection unit 16. The control unit 18 can include one or more sensors 24, such as proximity sensors or switches, which can communicate with the controller 20. The sensors 24 can detect, for example, a position of the fragrance unit 12. The controller 20, motor 22, and/or sensors 24 and motor can receive electric energy from a power supply, such batteries, a plug or hardwired electrical connection, or otherwise.

The dispenser 10 can be configured to indicate a status to an observer, such as maintenance personnel. The status can be, for example, that the fragrance unit 12 is due for replacement. In certain implementations, the change in status is indicated by a change in the position of the fragrance unit 12 within the dispenser 10. For example, when due for replacement, the fragrance unit 12 can be released from the connection unit 16, which causes the fragrance unit 12 to drop downward. As illustrated, a portion of the fragrance unit 12 can protrude from a bottom of the dispenser 10. In certain implementations, the fragrance unit 12 moves from a non-protruding position to a protruding position, or increases the amount by which the fragrance unit 12 protrudes out of the housing. In some variants, the fragrance unit 12 is moved by force of gravity and/or by a biasing force, such as from a spring. An observer can easily see that fragrance unit 12 has changed position and thus readily identify the status of the dispenser 10. For example, the observer can readily see whether the fragrance unit 12 is due for replacement.

II. Dispenser 110

FIGS. 2-12H illustrate another embodiment of a dispenser 110. The dispenser 110 resembles and/or can include any of the features of the dispenser 10. Reference numerals used to identify like features are incremented by a factor of one hundred. This numbering convention generally applies throughout this disclosure. Any component or step disclosed in any embodiment in this specification can be used in other embodiments.

Figure 2:
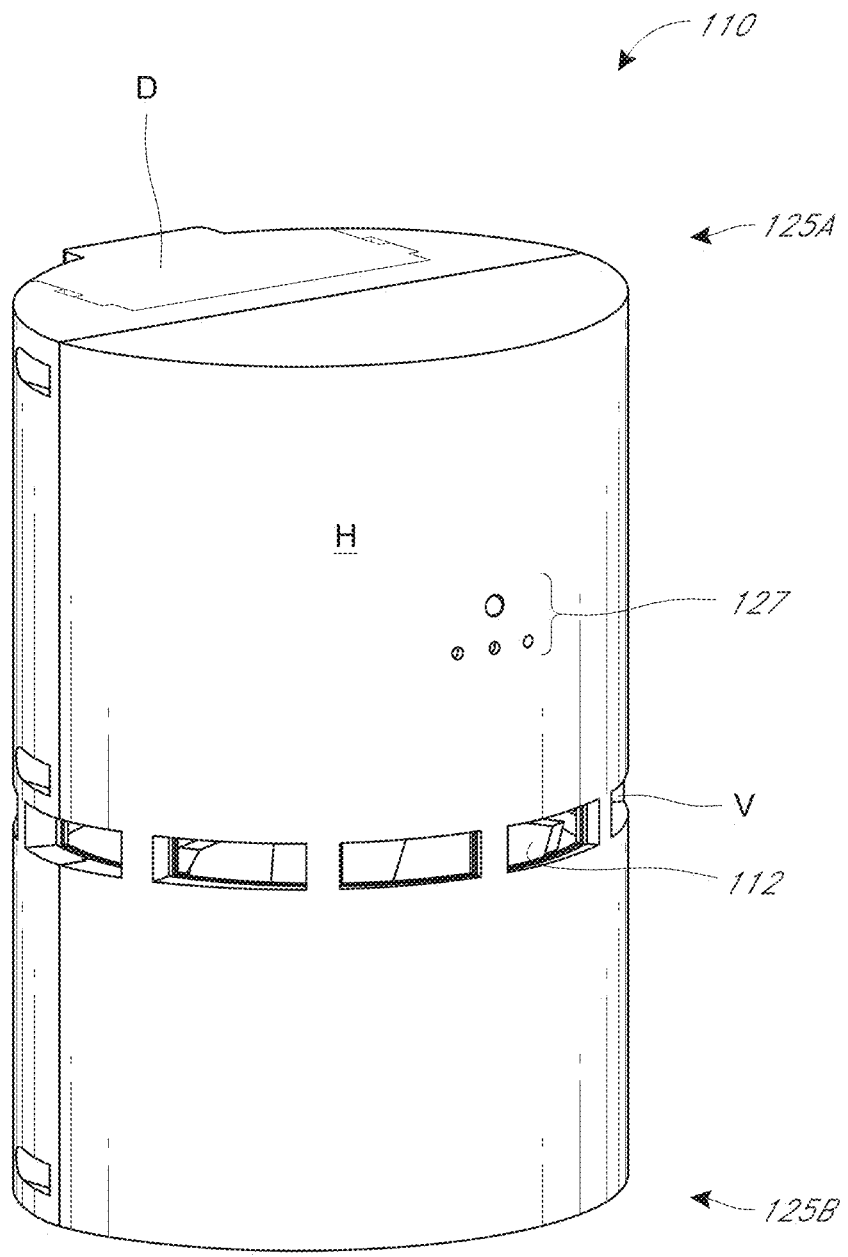
FIG. 2 illustrates another fragrance dispenser.

As illustrated in FIG. 2, the dispenser 110 includes a housing H, such as a hard plastic or metal outer casing or other protective cover. The dispenser 110 can be configured to mount on a wall. The dispenser 110 can have an upper end 125A and a lower end 125B. The dispenser 110 can include one or more vents V, which can facilitate airflow into and/or out of the dispenser 110. The dispenser 110 can have an indicator unit 127, such as lights.

Figure 3:
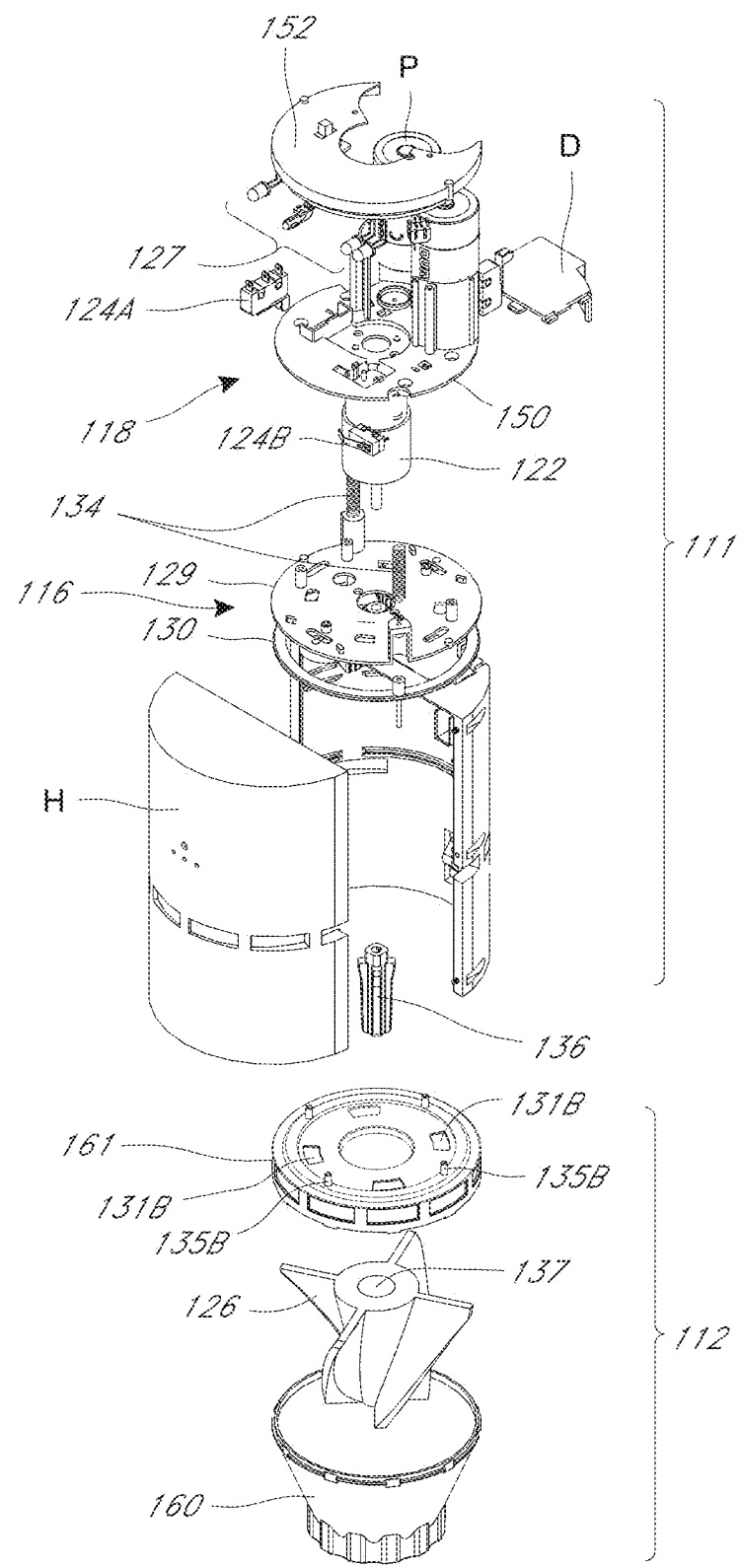
FIG. 3 illustrates an exploded view of the dispenser of FIG. 2.
Figure 4:
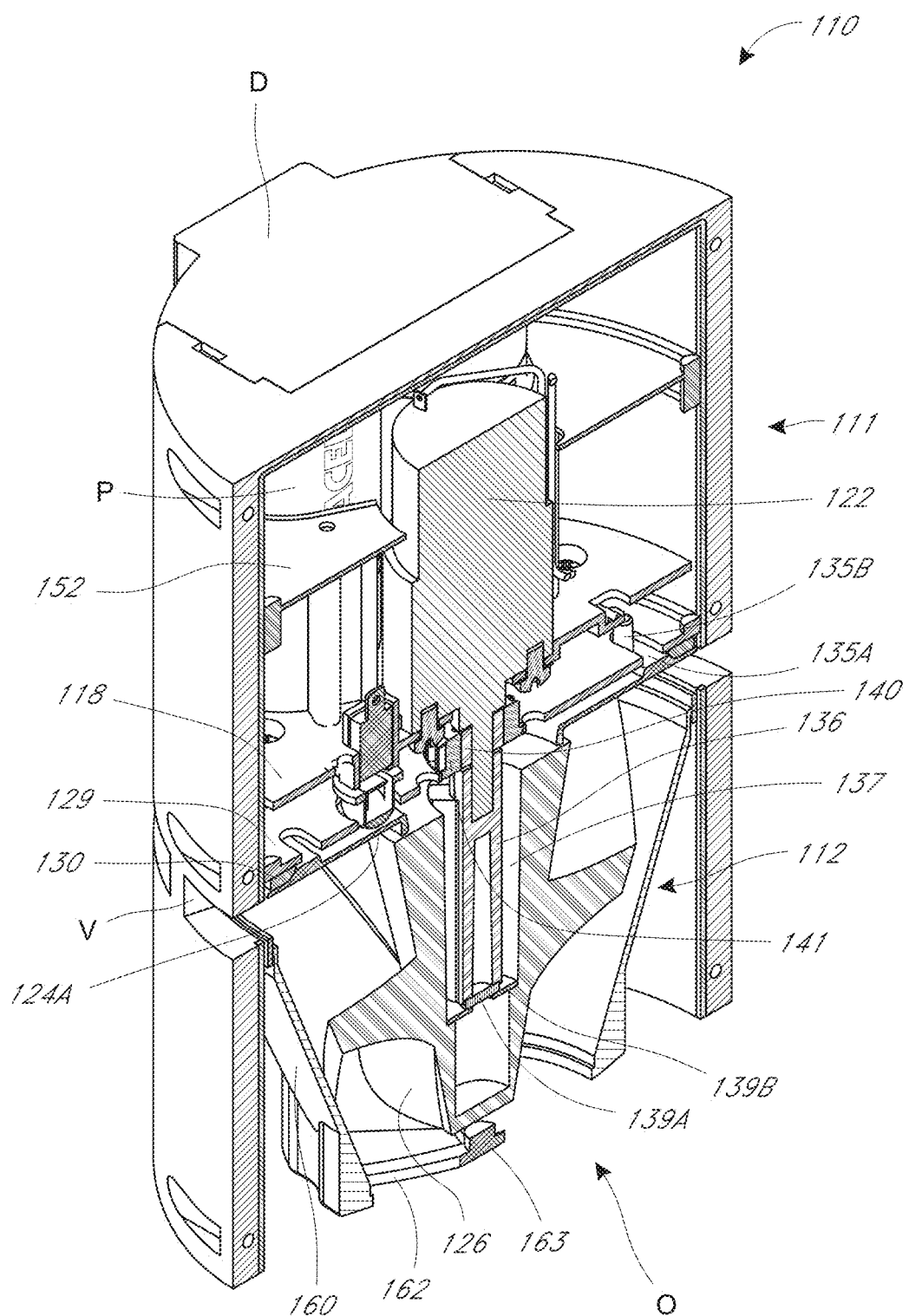
FIG. 4 illustrates a cross-sectional view of the dispenser of FIG. 2.

As shown in the exploded view of FIG. 3, and the cross-sectional view of FIG. 4, the dispenser 110 can include a core unit 111 and a cartridge 112. The cartridge 112 can be received in the housing H. For example, the cartridge 112 can be inserted into a chamber in the lower end 125B (e.g., bottom) of the dispenser 110. In certain implementations, the housing H is configured to interact with the cartridge 112. For example, the housing H can have a catch 128 that engages with the cartridge 112 when the cartridge 112 disengages from (e.g., drops from) the core unit 111, as discussed below. The catch 128 can retain the cartridge 112 in a disengaged position. In some embodiments, the catch 128 comprises an arm or a flange.

The dispenser 110 can include a motor 122, such as an electric motor. The motor 122 can drive an impeller 126 of the cartridge 112. The motor 122 can be positioned above the cartridge 112. The motor 122 can be a direct drive or indirect drive (e.g., with a transmission device, such as a belt, geartrain, etc.). The motor 122 and other components of the dispenser 10 can receive electric power from a power supply P. As shown, the power supply P can comprise one or more single-use or rechargeable batteries. In some variants, the power supply P comprises a wall outlet plug, solar cell, capacitor, or otherwise. The housing H can have a door D, which can provide access to the power supply, such as to enable replacement of the batteries.

In some implementations, the housing H has features that orient the cartridge 112 relative to the connection unit 116. For example, the housing H and cartridge 112 can be keyed such that the cartridge 112 can be inserted into the housing H in only certain orientations. This can aid in co-locating mating features of the cartridge 112 and core unit 111, which are discussed below.

In various embodiments, the dispenser 110 is configured to automatically indicate a status of the cartridge 112. For example, the cartridge 112 can move from an engaged position (see FIG. 5A) to a disengaged position (see FIG. 5B) in response to the cartridge 112 being ready for replacement. As illustrated, in the disengaged position, the cartridge 112 can protrude, or can increase the amount of the cartridge 112 that protrudes, from a bottom of the housing H. This can be readily seen by an outside observer, such as a maintenance person, and thus communicate to the observer whether the cartridge 112 is ready for replacement. The indication can occur without the observer needing to physically contact the dispenser 110 (e.g., without opening a door on the dispenser) and/or with the observer being remote from the dispenser (e.g., on an opposite side of a room that the dispenser 110 is located in).

II.A. Core Unit

FIGS. 2-11 illustrate an example of the core unit 111 (coupled or associated with the cartridge 112 in certain figures). The core unit 111 can be positioned in the housing H. For example, the core unit 11 can be permanently mounted in the housing H.

The core unit 111 can include a connection unit 116 and a control unit 118. The connection unit 116 can removably couple with the cartridge 112. The connection unit 116 can be biased to disengage from the cartridge 112. The control unit 118 can control various operations of the dispenser 110.

II.A.1. Connection Unit

The connection unit 116 can include a support element 129 and an engagement element 130. As discussed in more detail below, in certain embodiments, the support element 129 is configured to be stationary relative to the housing H and/or the engagement element 130 is configured to move (e.g., slide) relative to the support element 129. For example, the engagement element 130 can be configured to push the cartridge 112 away from the support element 129.

The support element 129 can comprise a rigid plate, disk, or other shape of material. The support element 129 can be adapted to couple to and/or secure the cartridge 112. In some embodiments, the support element 129 has one or more first securing features 131A, such as hooks, arms, male elements, or otherwise. The first securing features 131A can project downward from the support element 129. The support element 129 can include one or more tracks 132, such as channels. The support element 129 can include one or more first positioning features 135A. In some embodiments, the first positioning features 135A comprise slots (e.g., elongate through holes), female elements, or otherwise. The illustrated embodiment has four first securing features 131A and four first positioning features 135A, but other numbers are contemplated, such as one, two, three, five, six, or more. In some embodiments, the number of first securing features 131A is equal to the number of first positioning features 135A. In certain variants, the number of first securing features 131A is different from the number of first positioning features 135A. As illustrated, in certain embodiments, the first securing features 131A and first positioning features 135A are interspersed in an alternating manner in a circumferential direction.

In some implementations, the first securing features 131A of the support element 129 are configured to engage with second securing features 131B of the cartridge 112, such as apertures, female elements, etc. (see FIG. 3). For example, the first securing features 131A can engage (e.g., be received in) the second securing features 131B. In some embodiments, the first and second securing features 131A, 131B comprise a bayonet connection mechanism. After the securing features 131A, 131B have engaged, the cartridge 112 can be rotated relative to the support element 129. This can move a portion of the first securing features 131A (e.g., hooks) out of alignment with the second securing features 131B, thereby providing a physical interference between the first securing features 131A and the cartridge 112. In some embodiments, force from one or more biasing members 134 is applied to the cartridge 112, but the cartridge 112 is maintained in position by the first securing features 131A (e.g., the hooks engaged with a lid of the cartridge 112). The cartridge 112 can thus be coupled and/or secured to the support element 129.

In certain implementations, the first positioning features 135A of the support element 129 are configured to engage with second positioning features 135B of the cartridge 112, such as posts, male elements, etc. (see FIG. 3). For example, the first positioning features 135A can engage (e.g., receive)

the second positioning features 135B of the cartridge 112. In some embodiments, the first and second positioning features 135A, 135B comprise a slot and pin. In some embodiments, the pin can be configured to slide in the slot as the cartridge 112 is rotated relative to the support element 129.

In some implementations, the support element 129 includes a torque transmission element, such as a shaft 136. As illustrated, the shaft 136 can project downward, such as generally vertically downward. The shaft 136 can be centrally located on the support element 129. The torque transmission element can operably connect to the cartridge 112 to transmit motive force to the cartridge 112. For example, the shaft 136 can be configured to be received in a corresponding cavity 137 in the cartridge 112.

In some embodiments, the shaft 136 includes one or more alignment features, such as flanges 138. In some embodiments, the flanges 138 comprise radially extending wings. In some embodiments, the flanges 138 can taper outward, such as at an upper end, as illustrated. The flanges 138 can facilitate aligning and/or centering the cartridge 112 onto the shaft 136. For example, the flanges 138 can aid in positioning the cartridge 112 such that an axis of rotation of the impeller 126 of the cartridge 112 is substantially collinear with an axis of rotation of the shaft 136.

The shaft 136 can couple to the impeller 126. In some embodiments, the shaft 136 includes a first connecting element 139A, such as a magnet. The first connecting element 139A can be positioned on a bottom and/or free end of the shaft 136. The first connecting element 139A can be removably coupled with a second connecting element 139B (e.g., a metal washer) of the cartridge 112.

The shaft 136 can couple to the motor 122. For example, an output drive shaft of the motor 122 can be received in an upper end of the shaft 136 such that rotational motion from the motor 122 is transferred into the shaft 136. In some implementations, the motor 122 can rotate the output drive shaft in clockwise and counterclockwise directions. The shaft 136 and motor 122 can be coupled with a one-way connection 140, such as a one-way clutch, bearing, bushing, or other one-way torque transmission device. The one-way connection 140 can activate in only one rotational direction. This can permit rotation from the motor 122 to be transferred to the shaft 136 in one rotational direction (e.g., counterclockwise) but not in the other direction (e.g., clockwise). In several implementations, rotation of the motor 122 in a first direction spins the impeller 126 and/or rotation of the motor 122 in a second direction disengages the cartridge 112 from the connection unit 116.

Figure 9:
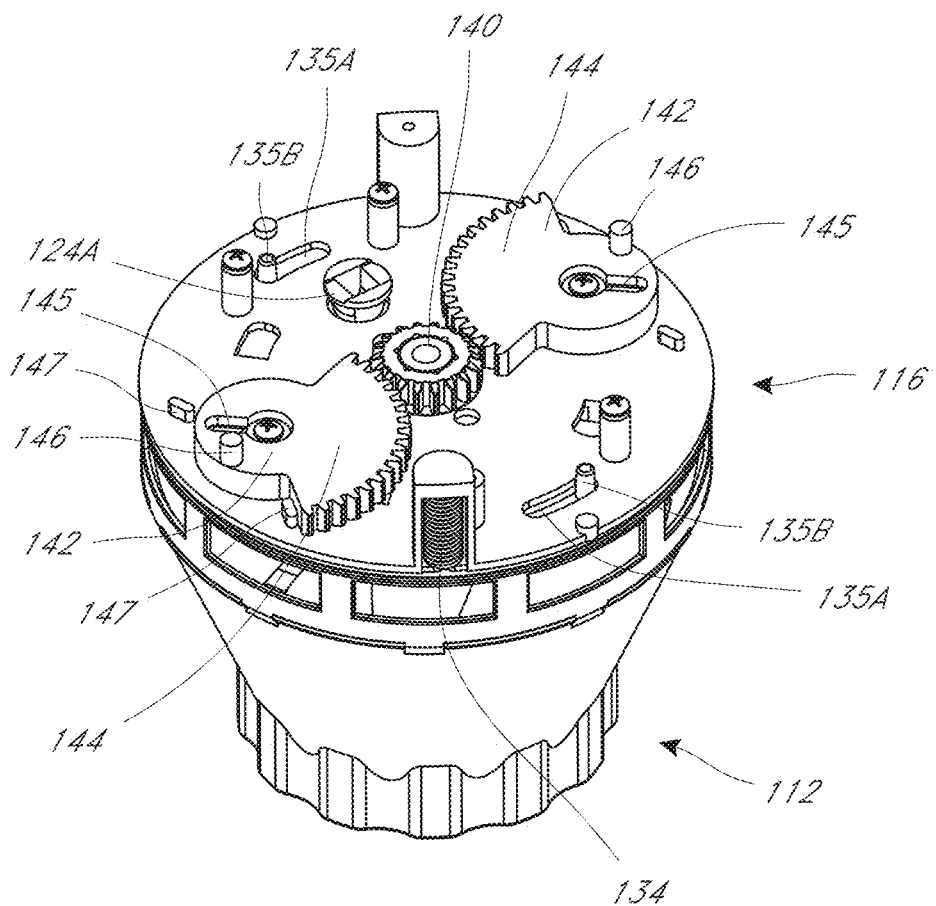
FIG. 9 illustrates portions of the connection unit and cartridge.

In some embodiments, the shaft 136 is connected to a gear 141 (e.g., a spur gear) or other torque transfer element, such as via the one-way connection 140. The gear 141 can be connected to one or more control gears 142. As shown in FIG. 9, the control gear 142 can include a smaller body portion 143 that includes the axis of rotation of the control gear 142 and a larger toothed portion 144. The toothed portion 144 can engage with the gear 141. In some implementations, the toothed portion 144 extends only around a portion of the periphery of the control gear 142, such as at least about: 90°, 120°, 150°, or more.

The control gear 142 can include one or more cartridge interface features, such as holes 145 (e.g., through holes). In certain implementations, when the first and second positioning features 135A, 135B are engaged (e.g., the posts protrude through the slots), the second positioning features 135B of the cartridge 112 extends into the holes 145 of the control gears 142. The position of the cartridge 112 can thus be affected by the position of the control gear 142. For example, in an embodiment in which the first and second positioning features 135A, 135B comprise a slot and pin, rotating the control gear 142 in a first direction (e.g., counterclockwise) to a first rotational position can move the pin to one end of the slot and/or rotating the control gear 142 in a second direction (e.g., clockwise) to a second rotational position can move the pin to the other end of the slot. The control gear 142 can include a position indicator 146, such as a peg. Movement of the control gear 142 can be limited by stops 147 on the support element 129.

Figure 5A:
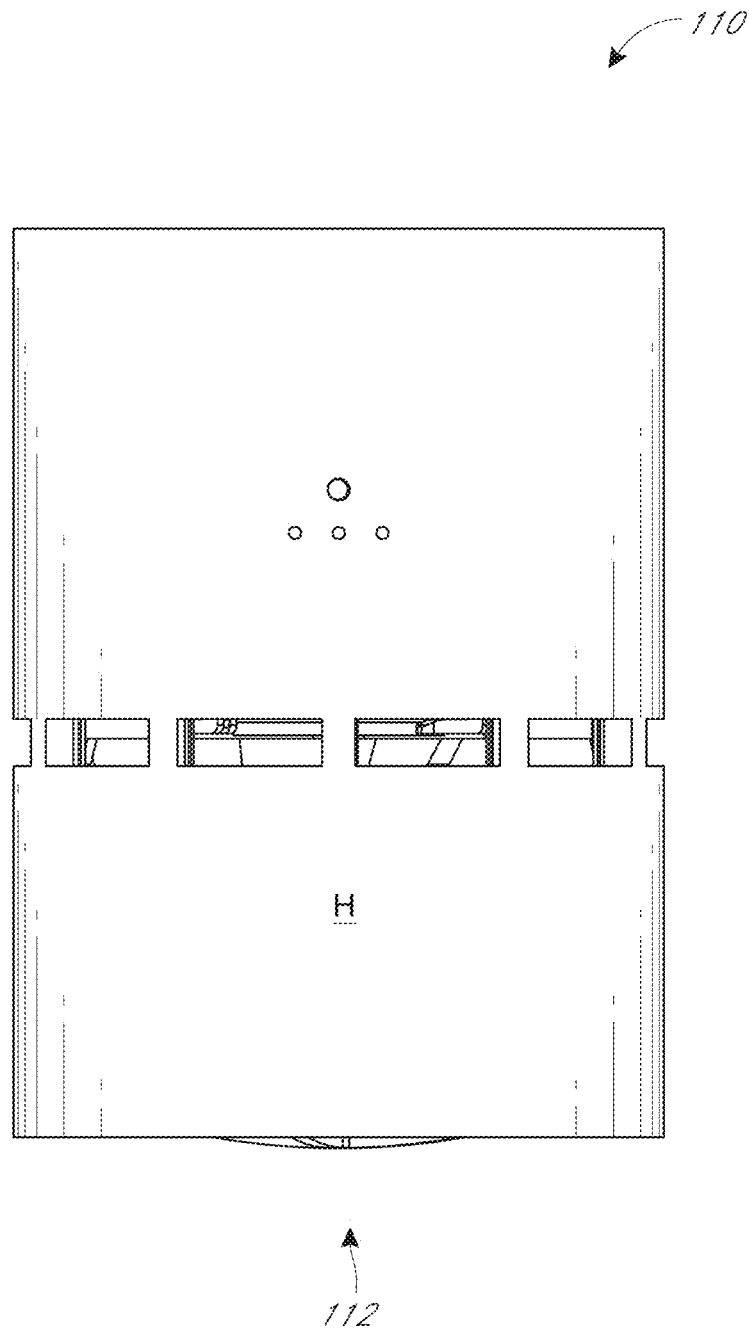
FIGS. 5A and 5B illustrate a front view of the dispenser of FIG. 2 with a cartridge in an engaged position and a disengaged position, respectively.
Figure 5B:
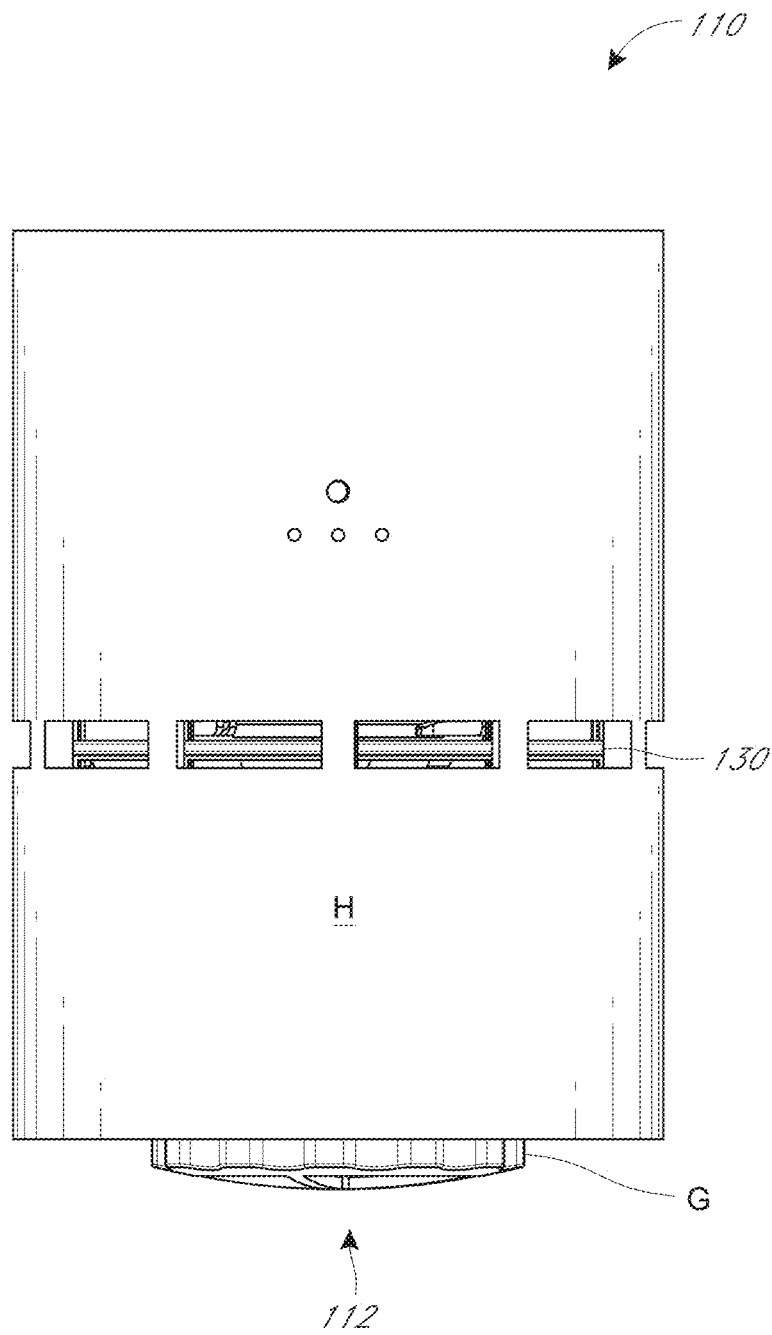
Figure 6:
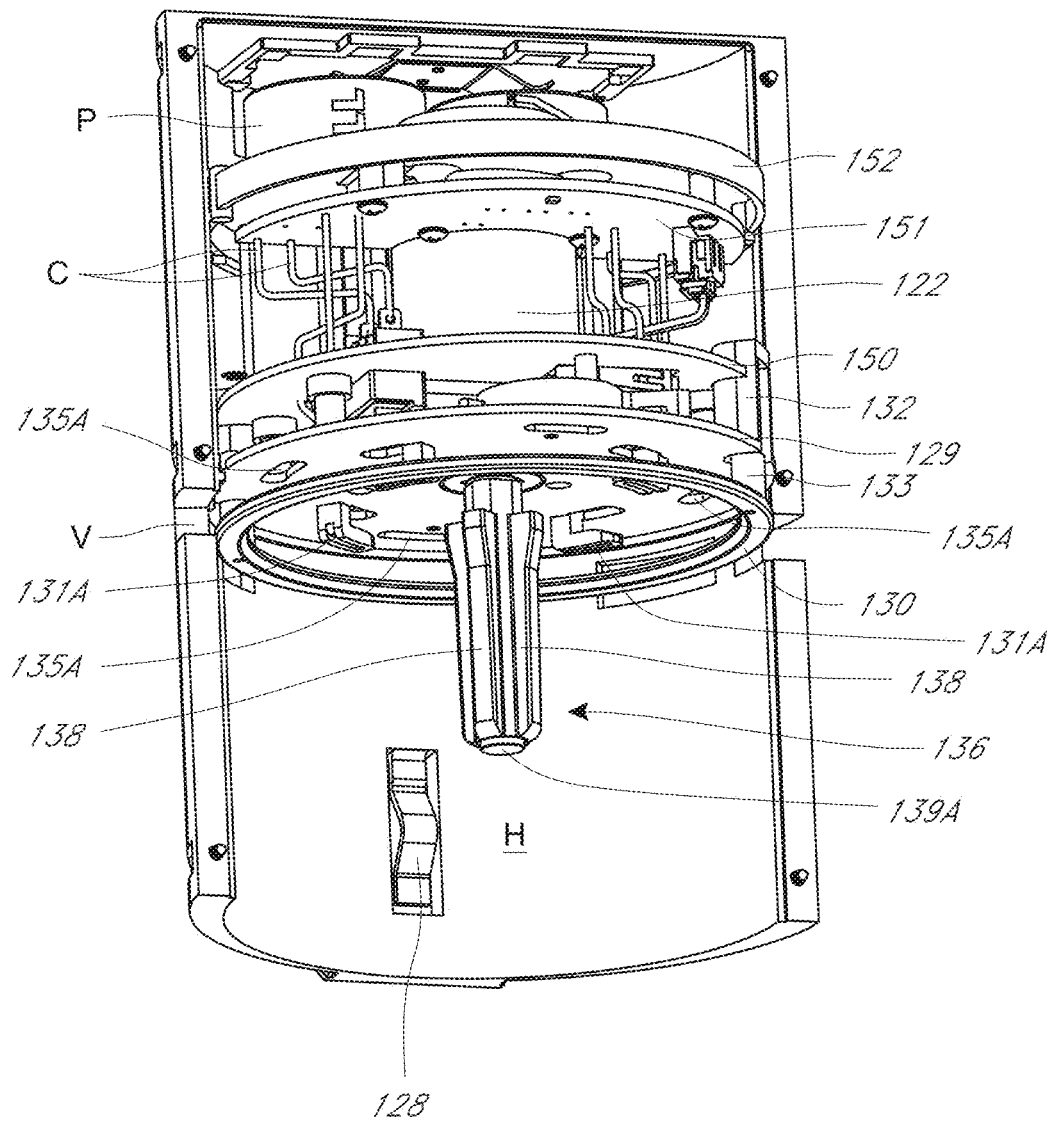
FIG. 6 illustrates a rear housing and a core unit of the dispenser of FIG. 2.
Figure 7:
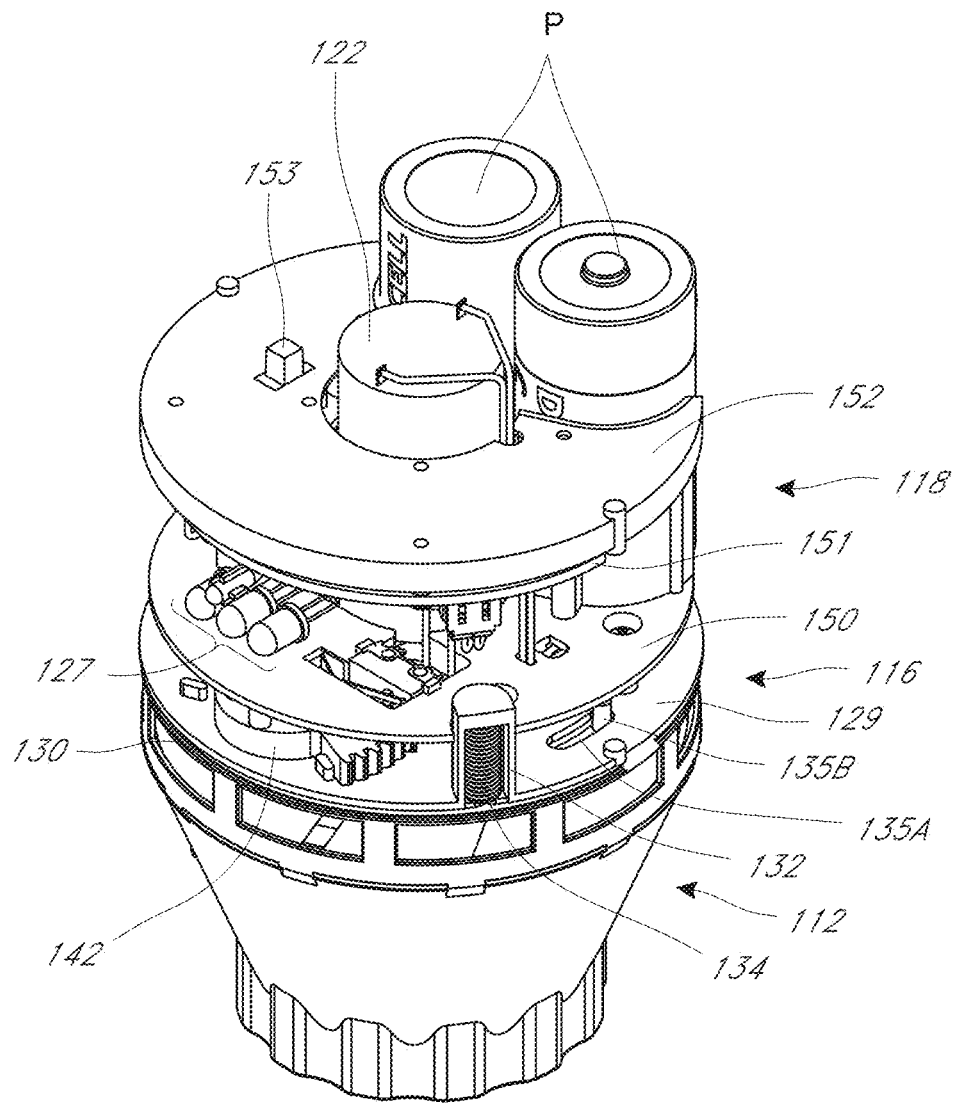
FIG. 7 illustrates the core unit connected with the cartridge, the core unit comprising a control unit and a connection unit.
Figure 8:
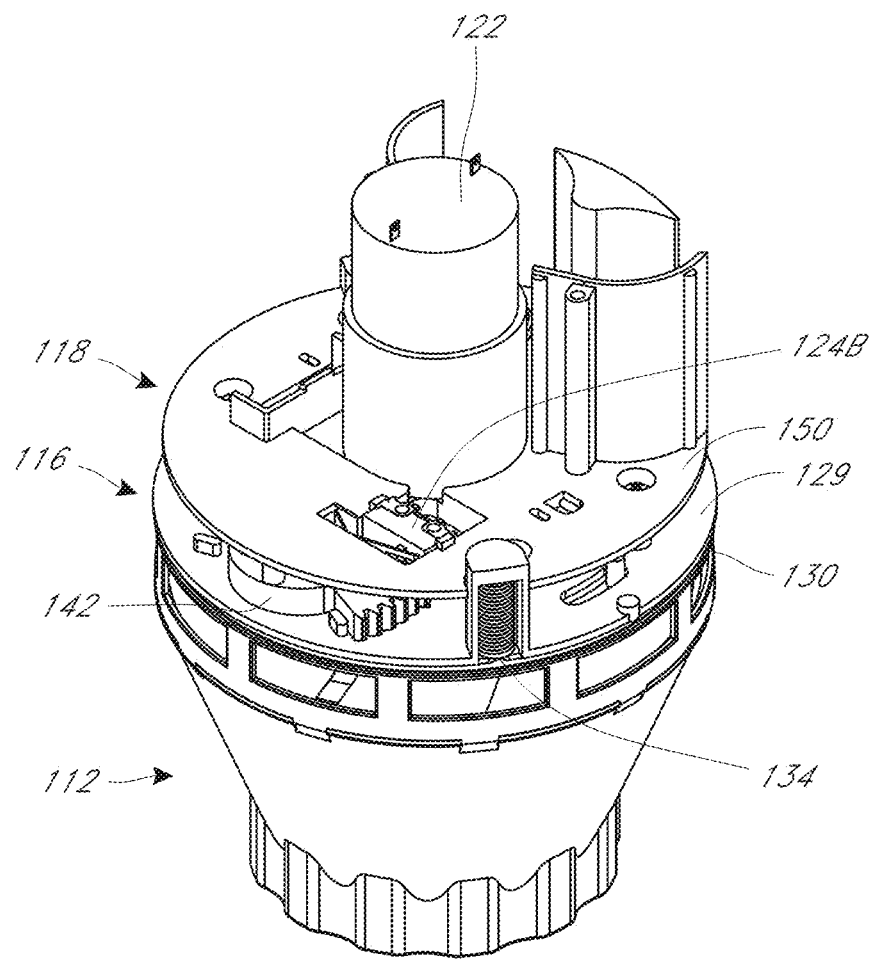
FIG. 8 illustrates portions of the control unit, connection unit, and cartridge.

The engagement element 130 can be positioned below the support element 129. In certain implementations, the engagement element 130 comprises an annular member, such as a ring. As illustrated, in some embodiments, the engagement element 130 is radially outward and/or surrounds the first securing features 131A and/or the first positioning features 135A. When the cartridge 112 is not installed in the housing H and/or when the cartridge 112 has been dropped to the disengaged position, which may indicate that the cartridge 112 is due for replacement, the engagement element 130 can be visible through the vent V. For example, as shown in FIG. 5B, the engagement element 130 can be generally horizontally positioned in and/or aligned with at least one of the vents V. The engagement element 130 can be brightly colored (e.g., yellow, orange, red, etc.) or otherwise provide a visual signal that the cartridge 112 is not present or is in the disengaged position.

The engagement element 130 can include guides 133, such as arms, which can project upwardly. The guides 133 can be received in a corresponding one of the tracks 132. One or multiple biasing members 134, such as springs, can be positioned between the support element 129 and an engagement element 130. For example, the biasing members 134 can be positioned over a respective one of the guides 133 and/or in a respective one of the tracks 132. The biasing member 134 can bias the engagement element 130 away from the support element 129.

The engagement element 130 can be adapted to engage with an upper portion of the cartridge 112. For example, when the cartridge 112 is inserted into the dispenser 110, the cartridge 112 can abut against the engagement element 130. With continued upward force on the cartridge 112, the cartridge 112 and engagement element 130 can be moved against the bias of the biasing member 134. This can energize the biasing member 134. In some embodiments, the cartridge 112 is pushed upward until the engagement element 130 is stopped by the support element 129. In certain variants, an upper stop on the housing H limits upward travel of the engagement element 130. A lower stop on the support element 129 or housing H can limit downward travel of the engagement element 130.

II.A.2 Control Unit

As mentioned above, the core unit 111 can include the control unit 118. The control unit 118 can be positioned above the connection unit 116. In some embodiments, the motor 122 protrudes through the control unit 118, such as through a central portion of the control unit 118 as illustrated. The control unit 118 can include a base 150 that couples to and supports the motor 122. The base 150 can be rigid, such as made of metal or hard plastic. The base 150 can include recesses that receive the tracks 132.

In some embodiments, the control unit 118 includes an electronic controller, such as a processor and memory. The controller can be positioned on a printed circuit board (PCB) 151. The control unit 118 can include a cover 152, which can protect and/or cover a top portion of the PCB 151. For example, when the door D is opened, the cover 152 can protect the PCB 151. The cover 152 can be made of metal, hard plastic, or another rigid material. A power switch 153 or other user interface can extend through the cover 152.

The control unit 118 can include one or more sensors 124. The sensors 124 can be, for example, switches, proximity sensors, or otherwise. In some embodiments, the control unit 118 includes an installation sensor that detects whether the housing H is installed on a wall or other structure. The dispenser 110 can be configured to not operate when not installed.

In certain implementations, the control unit 118 has an occupancy sensor, such as a photosensor, motion sensor, or otherwise. This can enable the dispenser 110 to determine whether the space in which the dispenser 110 is located is occupied. For example, in an embodiment in which the occupancy sensor comprises a photosensor, detecting that the space is dark can indicate that the space is likely unoccupied. The dispenser 110 can be configured to change operation in response to information from the occupancy sensor. For example, the dispenser 110 can cease or slow spinning of the impeller 126 in response to determination that the space is unoccupied (e.g., dark).

In some embodiments, the control unit 118 has a cartridge present sensor 124A. The cartridge present sensor 124A can detect whether the cartridge 112 has been pushed up into engagement with the connection unit 116. In some embodiments, the cartridge present sensor 124A comprises a switch that is depressed by an upper portion of the cartridge 112, as shown in FIG. 4.

In certain embodiments, the control unit 118 has a cartridge secured sensor 124B. The cartridge secured sensor 124B can detect that the cartridge 112 has been secured to the connection unit 116, such as by being rotated relative to the support element 129 and/or by the first and second securing features 131A, 131B being mated to inhibit or prevent removal of the cartridge 112. In some embodiments, the cartridge secured sensor 124B comprises a switch that is depressed by the position indicator 146 and/or the second positioning element 135B, such as at or near an end of the pin sliding in the slot as the cartridge 112 is rotated relative to the support element 129.

The control unit 118 can include various conductors C, such as wires, traces, or otherwise. The conductors C can connect various electric elements of the dispenser 110, for example, the conductors C can connect the controller to the power supply P, motor 122, sensors 124, controller, and otherwise.

The control unit 118 can include an indicator unit 127, such as a plurality of lights. In some embodiments, the indicator unit 127 includes a power status light that indicates (e.g., illuminates) when the dispenser 110 has electric power. The power status light can indicate, such as by flashing, when the power supply is low (e.g., when the batteries are due for replacement). The indicator unit 127 can include a cartridge present light, which can indicate (e.g., illuminate) when the cartridge 112 is pushed up into engagement with the connection unit 116. The indicator unit 127 can include a cartridge secured light, which can indicate (e.g., illuminate) when the cartridge 112 is secured with the connection unit 116. In certain implementations, the cartridge present light and cartridge secured light are the same light, but with different colors to indicate the different statuses. Some implementations include a cartridge disengaged light, such as a light that illuminates in response to the dispenser 110 disengaging the cartridge 112 from the connection unit 116 and/or dropping the cartridge 112 to the disengaged position. This can signify to a maintenance or other person that the cartridge 112 is due for replacement.

II.B Cartridge

FIGS. 12A-12H illustrate an example of the cartridge 112. The cartridge 112 includes a fragrance reservoir 114 (also called a fragrance composition), which can include a fragrance liquid, such as a fragrance oil. The fragrance liquid can be suitable for use with plastics with sustained release and/or evaporation rate-vapor pressure. The cartridge 112 can be configured to reduce the chance of a person touching the fragrance reservoir 114, which could cause damage to the reservoir 114 or apply the fragrance liquid directly to the person. For example, the fragrance reservoir 114 can be enclosed in the cartridge 112.

The fragrance reservoir 114 can include a substrate (also called a support structure) that the fragrance liquid is contained or embedded in or on. In some embodiments, the substrate comprises a lattice. The substrate can comprise a plurality of cells or chambers, such as interstitial spaces. The chambers can be in fluid communication. The chambers can receive the fragrance liquid. The substrate can be configured to facilitate movement of the fragrance liquid through the chambers. For example, the fragrance liquid can move from inner chambers to outer chambers in the substrate, thereby enabling the fragrance liquid to migrate to a location to escape the substrate (e.g., due to evaporation) to provide fragrance to a surrounding environment.

The substrate can have a yielding, porous, and/or fibrous skeleton or framework. For example, the substrate can have a spongy texture and/or resiliency. In some embodiments, the substrate comprises thermoplastic elastomer (TPE) and/or ethylene-vinyl acetate (EVA) resin. In certain implementations, the substrate comprises a thermoplastic elastomer composition comprising a blend of hydrogenated styrenic block copolymer and a plasticizer (e.g., paraffinic or naphthenic) that is compatible with the mid-blocks of the hydrogenated styrenic block copolymer. The hydrogenated styrenic block copolymer can comprise a polyolefin. In some variants, the TPE comprises olefinic block copolymers, thermoplastic urethane, coplysters, and coplyamides. In certain implementations, the substrate is comprised of gums (e.g., cellulose gum), gellers or thickeners (e.g., carrageenan), polymers, or other materials. In some embodiments, the framework is hydrophilic. In certain variants, the framework is hydrophobic.

In some embodiments, the fragrance reservoir 114 includes hydrophilic and/or diffusion agents. For example, the fragrance reservoir 114 can include a powdered or beaded blend of amorphous silicon dioxide (e.g., silica and fumed silica) with optimal surface area and alumino silicate (e.g., zeolite) and/or inorganic fillers and/or EVA polymer binder. In certain implementations, using a TPE or EVA resin as a base, fillers are added to create a porous hydrophilic or resin. In some cases, a hydrophobic cell structure may be desirable.

Various proportions of the substrate to other components (e.g., the combination of the liquid fragrance, a foamer, and/or a hydrophilic agent) are contemplated. In some implementations, the other components comprise 15% or greater by weight and/or the base resin comprises 85% or less by weight. In some implementations, the other components comprise 30% or greater by weight and/or the base resin comprises 70% or less by weight. In certain embodiments, the substrate comprises at least about 80% by weight of the fragrance reservoir 114. In some variants, the substrate comprises less than or equal to about 80% by weight of the fragrance reservoir 114.

In some implementations, the substrate comprises a material that has been foamed. For example, the substrate can be formed by adding a foamer to a base resin (such as the materials described above). The foamer can comprise chemical foaming agents that include, for example, blends or individual chemicals of isocyanate and water, azodicarbonamide, hydrazine, and sodium bicarbonate. The action of the foamer can create the chambers in the substrate. In certain embodiments, the foamer comprises azobisisobutyronitrile (AIBN).

The fragrance reservoir 114 can be contained in a casing, such as a hard plastic case. The casing can include a shell 160 and a lid 161. The shell 160 can comprise a taper such that an upper portion is wider than a lower portion. A lower end (e.g., bottom) of the shell 160 can include a grip G, such as ribs, knurling, a handle, etc. When the cartridge 112 is in the disengaged position, the grip can protrude out of the housing H. The grip can provide a convenient location to grasp the cartridge 112, such as during installation and/or removal from the housing H. The shell 160 can have a lower opening O. In some embodiments, the lid 161 includes the vents V. The lid 161 can be configured to engage (e.g., abut) the engagement element 130. The lid 161 can be configured to receive the engagement element 130. For example, the lid 161 can include a groove that the engagement element 130 fits into when the cartridge 112 is connected with the support element 129. The groove and/or the engagement element 130 can be rounded or chamfered to facilitate guiding the engagement element 130 into the groove. The lid 161 can have windows W. The windows W align with and/or be in fluid communication with the vents V. In some embodiments, air can enter the opening O, pass over and/or around the fragrance reservoir 114, and exit through the windows W and vents V. In some variants, air can enter the vents V and windows W, pass over and/or around the fragrance reservoir 114, and exit through the opening O.

The shell 160 can have one or more struts 162, such as ribs. The struts 162 can protrude into the opening O. The struts can include a stop 163, such as at the intersection of the struts 163. The stop 163 can limit downward travel of the impeller 126 relative to the shell 160. See FIG. 11.

The fragrance reservoir 114 can include the impeller 126. For example, some or all of the fragrance reservoir 114 can be molded or otherwise formed into an impeller shape. The impeller 126 can include a plurality of blades. The blades can be configured to facilitate airflow over the fragrance reservoir 114, thereby dispensing some of the fragrance to the air. As mentioned above, the impeller 126 can include the cavity 137, which can be configured to receive the shaft 136. In some embodiments, the cavity 137 extends at least about half of the height of the impeller 126. In some embodiments, the impeller 126 is hollow though some, most, or all of its axial height. The impeller 126 can be floating in the casing. For example, in certain variants, the impeller 126 can move within and relative to the casing, such as in the axial direction.

The impeller 126 can include the second connecting element 139B, such as a metal washer. As illustrated, in some embodiments, the second connecting element 139B is positioned in a bottom end of the cavity 137. The impeller 126 can include a step or other feature that supports the second connecting element 139B.

II.C Operation

In use, the cartridge 112 can be positioned under the housing H. The cartridge 112 can be moved upward into the housing H. For example, the cartridge 112 can be passed through an opening in the bottom of the housing H. As mentioned above, the housing H can have features that orient the cartridge 112 relative to the connection unit 116. For example, the housing H and cartridge 112 can be keyed such that the cartridge 112 can be inserted into the housing H in only certain orientations. This can aid in co-locating mating features of the cartridge 112 and core unit 111, such as the securing features 131A, 131B and/or the positioning features 135A, 135B.

In some embodiments, the shaft 136 is received in the cavity 137 of the cartridge 112. The shaft 136 can interface with walls of the cavity 137, thereby aligning the cartridge 112 with the shaft 136 and/or other portions of the core unit 111. For example, an axial centerline of the impeller 126 can be substantially aligned with (e.g., substantially collinear with) an axial centerline of the shaft 136. The shaft 136 can be configured to engage with the walls of the cavity 137 in such a manner that rotation of the shaft 136 is transferred to the impeller 126. For example, the shaft 136 can be received in the cavity 137 with an interference fit. In some implementations, the shaft 136 is resilient and/or configured to compress within the walls of the cavity 137.

The cartridge 112 can be engaged with the engagement element 130. For example, the cartridge 112 can be pressed against the engagement element 130. The cartridge 112 and engagement element 130 can be moved upward as a unit. This can compress or otherwise energize the biasing member 134. In certain variants, the engagement element 130 is moved to abut against the support element 129 or a stop on the housing H.

In some embodiments, the positioning features 135A, 135B interface. For example, the first positioning features 135A (e.g., slots) of the support element 129 can receive the second positioning features 135B (e.g., posts) of the cartridge 112. The posts 135B can be positioned at an end of the slots. The positioning features 135A, 135B can aid in properly orienting the cartridge 112 relative to the support element 129.

In certain embodiments, the second positioning features 135B are received in the respective holes 145 in the control gears 142. For example, the posts on the cartridge 112 can protrude through the slots in the support element 129 and extend into the holes 145 of the control gears 142. The control gears 142 can be in a first position. The first position of the control gears 142 can be called an "unsecured position" because, in this position, the cartridge 112 is not secured to the connection unit 116 (e.g., if released by the user the cartridge 112 can be pushed away from the support element 129 by the biasing member 134).

Figure 10:
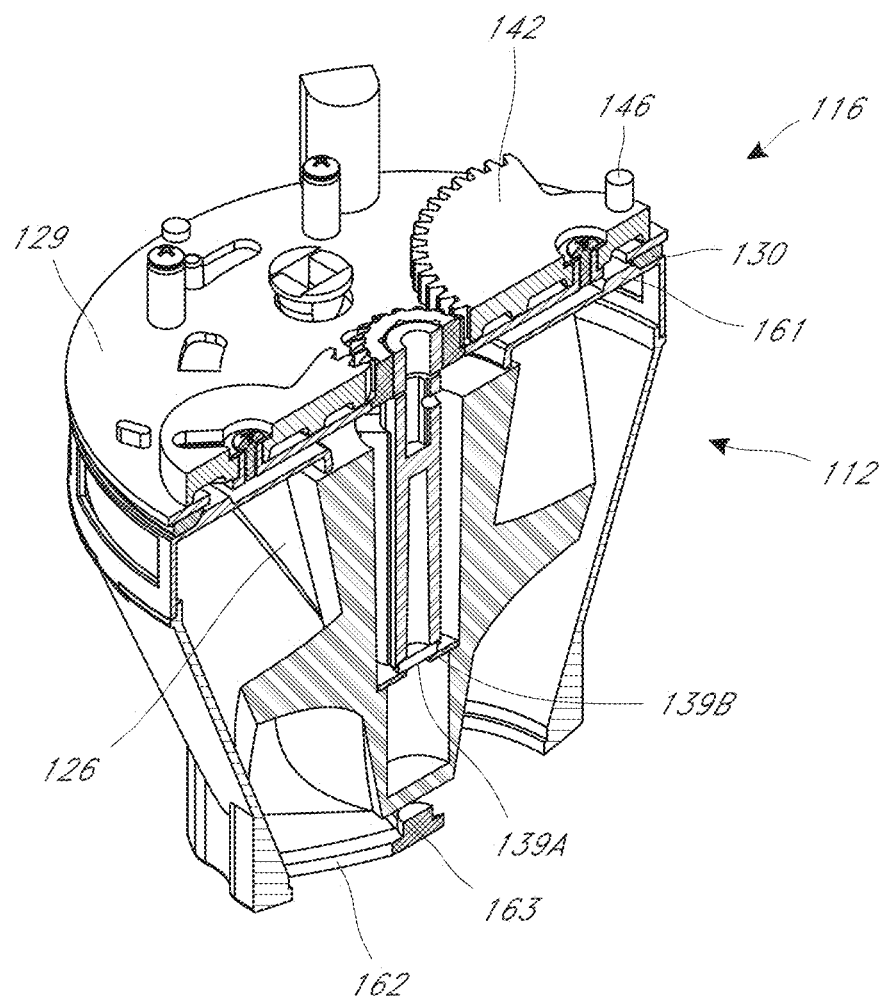
FIGS. 10 and 11 illustrate a cross-sectional view of portions of the connection unit and cartridge, with control gears in a secured position and an unsecured position, respectively.

In some implementations, the impeller 126 moves axially relative to the casing of the cartridge 112. For example, in response to the shaft 136 being inserted into the cavity 137, and/or the cartridge 112 being engaged with the connection unit 116, an attractive force between the first and second connecting elements 139A, 139B can move (e.g., pull) the impeller 126 upward. As shown in FIG. 10, the impeller 126 can be spaced apart from (e.g., suspended above) the stop 163. This can reduce friction on the impeller 126 or otherwise facilitate rotation of the impeller 126 in the casing. In some embodiments, the connection between the connecting elements 139A, 139B transfers torque between the shaft 136 and the impeller 126. In certain implementations, the movement of the impeller 126 occurs concurrent with or after the interfacing of the positioning features 135A, 135B.

In certain implementations, the securing features 131A, 131B can enter a first stage of engagement. For example, in the first stage of engagement, the first securing features 131A (e.g., hooks) of the connection unit 116 can be received in the second features 131B (e.g., apertures) of the cartridge 112. In certain implementations, the first stage of engagement of the securing features 131A, 131B occurs concurrent with or after the interfacing of the positioning features 135A, 135B. In some embodiments, when the securing features 131A, 131B are in the first stage of engagement, the cartridge 112 can be readily separated from the connection unit 116.

The cartridge 112 can secured to the support element 129. This can comprise moving the securing features 131A, 131B into a second stage of engagement. For example, in some embodiments, the cartridge 112 is rotated relative to the support element 129 and/or the engagement element 130. The securing features 131A, 131B can move relative to each other. For example, in the illustrated embodiment, the hooks can slide within the apertures 131B. This can move an end portion of the hooks out of alignment with the apertures 131B, thereby providing a physical interference between the first securing features 131A and the support element 129 in the axial direction. In some embodiments, when the securing features 131A, 131B are in the second stage of engagement, the cartridge 112 is inhibited or prevented from being separated from the connection unit 116. For example, the physical interference can stop the biasing member 134 from moving the cartridge 112 out of position (e.g., downward).

In certain implementations, the rotation of the cartridge 112 causes the positioning features 135A, 135B to move relative to each other. For example, in the illustrated embodiment, the posts of the cartridge 112 can slide in the slots of the support element 129, such as to an opposite end of the slots. In certain embodiments, because the posts are received in the respective holes 145 in the control gears 142, the movement of the posts causes the control gears 142 to rotate, such as to a second position. The second position of the control gears 142 can be called a "secured position" because, in this position, the cartridge 112 is secured to the support element 129, as discussed above. In some embodiments, rotation of the control gears 142 causes rotation of the gear 141.

In some embodiments, the controller can determine that the cartridge 112 has been properly installed, such as using information from one or more of the sensors 124A, 124B. At least partly in response, the controller can instruct the motor 122 to operate. For example, after detecting that the cartridge 112 is present and secure, the dispenser 110 can commence spinning the impeller 126. The motor can spin the shaft 136, which is transferred to the impeller 126. This can cause air to flow over the impeller 126 and then exit the dispenser 110, thereby providing fragrance to the ambient environment. In some embodiments, the dispenser 110 dispenses fragrance at least partly based on the occupancy sensor detecting that the space is occupied and/or has recently been occupied (e.g., within the at least about the last 10 minutes).

The control unit 118 can be configured to control various operations of the dispenser 110. For example, the control unit 118 can control operation of the motor 122, such as rotational speed, "on time," and/or activation frequency. The control unit 118 can be configured to balance fragrance distribution over the life of the cartridge 112. In some embodiments, the control unit 118 activates the motor 122 such that the impeller 126 rotates at a rotational speed for a period, stops for a period, and then repeats. In certain implementations, the amount of fragrance released is controlled at least in part by factors such as: the rate of impeller rotation, the period of impeller rotation, the frequency of impeller rotation (e.g., the time between periods), the type of fragrant material, and/or other factors. The control unit 118 can account for of these factors in directing operation of the dispenser 110.

The dispenser 110 can be configured to maintain a substantially constant level of fragrance in the environment. In some embodiments, the length of time that the motor 122 is operated (the run time) is a function of the age of the cartridge 112 (e.g., the length of time that the cartridge 122 has been installed in the dispenser 110). For example, the longer the cartridge 112 has been in the dispenser 110 the longer the motor 122 can be operated and/or the shorter the cartridge 112 has been in the dispenser 110 the shorter the motor 122 can be operated. This can compensate, for example, for the fragrance reservoir 114 becoming less full and/or less portent over time and/or with use. In some implementations, the run time for a dispensation cycle is directly tied to the age of the cartridge 112. The run time can be affected by other factors. For example, the run time can be affected by the type of fragrant material, as certain materials are more potent than others.

In some implementations, the dispenser 110 is configured to provide a desired service life. For example, the dispenser 110 can be configured to dispense scent, operate the motor 122, and/or perform other operations achieve a service life of about: 3 months, 6 months, 1 year, or otherwise. In some variants, the dispenser 110 is configured to receive (e.g., via an input device) or to determine an amount of available power or fragrance, such as in the battery or fragrance reservoir 114. The dispenser 110 can be configured to adjust operation based at least partly on the amount of available power or fragrance, such as to ration the power and/or fragrance to achieve a desired service time. In some embodiments, the cartridge 112 is configured to communicate a service life to the control unit 118. For example, the cartridge 112 can communicate via RFID or otherwise.

In some implementations, the dispenser 110 is configured to vary operation based at least partly on the size of the room that the dispenser 110 is installed in. In some embodiments, the dispenser 110 is configured to receive an input, such as via a switch on the control unit 118, regarding the size of the room. For example, the dispenser 110 can receive an input of whether the room is small or large. According to some embodiments, for a small room, the motor 122 is operated for less than or equal to about 15 seconds every cycle period (e.g., greater than or equal to about 30 minutes). In certain variants, for a large room, the motor 122 is operated for greater than or equal to about 25 seconds every cycle period (e.g., less than or equal to about 30 minutes).

The dispenser 110 can be adapted to disengage the cartridge 112 from the support element 129. This can occur, for example, in response to a period of use of the cartridge 112, number of uses of the cartridge 112, or other criteria. In various embodiments, the cartridge 112 can be disengaged when (e.g., in response to) a determination is made (e.g., by the controller) that the cartridge 112 has reached a depleted state. In some embodiments, the dispenser 110 determines that the cartridge 112 is depleted based on time. For example, based on the number of days or months since the cartridge 112 was engaged with (e.g., installed in) the connection unit 116. In certain implementations, the time is at least: 30 days, 60 days, 90 days, 180 days, or otherwise. In some implementations, a component of the dispenser 110, such as the controller, has a software-controlled timer that resets and/or activates when the cartridge 112 is inserted. The timer can be based at least partly on a "term" of the cartridge 112. The term can be programmed in the controller, such as being retained in non-transitory memory. The term can be based on, for example, the size and/or life of the cartridge that determines its useful life. The dispenser 110 can eject the cartridge 112 when the term is reached and/or the cartridge 112 is otherwise considered depleted. In some variants, the dispenser 110 determines that the cartridge 112 is depleted based on the length of time that the motor 122 has been on since the cartridge 112 was installed.

In some embodiments, during a disengagement operation, the motor 122 changes direction. As discussed above, during normal operation, the motor 122 spins the output drive shaft in a first rotational direction, and such rotation can be transferred to the shaft 136 and impeller 126. Because of the one-way connection 140, such rotation is not transferred to the gear 141. In some implementations, during the disengagement operation, the motor 122 reverses to spin the output drive shaft in the opposite rotational direction. This causes the one-way connection 140 (e.g., one-way clutch) to activate and thus transfer the motion to the gear 141. In turn, the gear 141 can cause the control gears 142 to rotate from the secured position toward the unsecured position. In certain implementations, when the motor 122 spins the output drive shaft in the opposite rotational direction, torque from the motor 122 is not transferred to the impeller 126 and/or the impeller 126 does not rotate.

Figure 11:
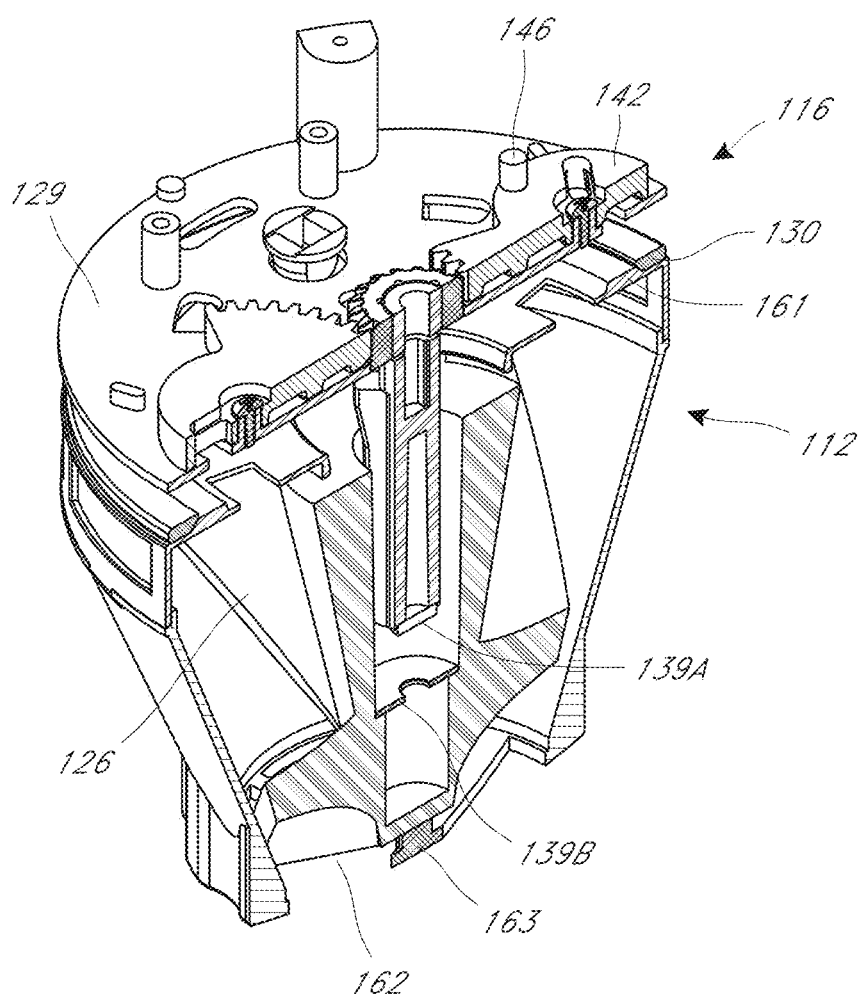
Figure 12A:
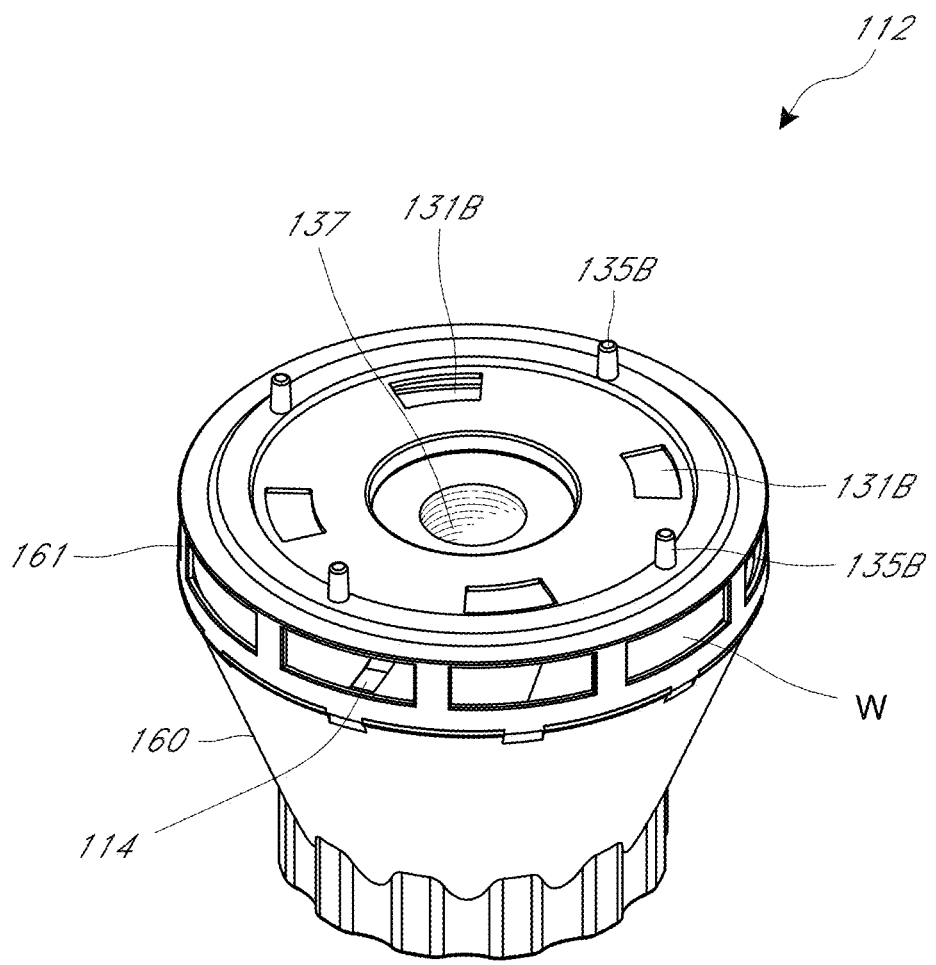
FIG. 12A-12H illustrate front perspective, bottom perspective, front, rear, left, right, top, and bottom views of the cartridge.
Figure 12B:
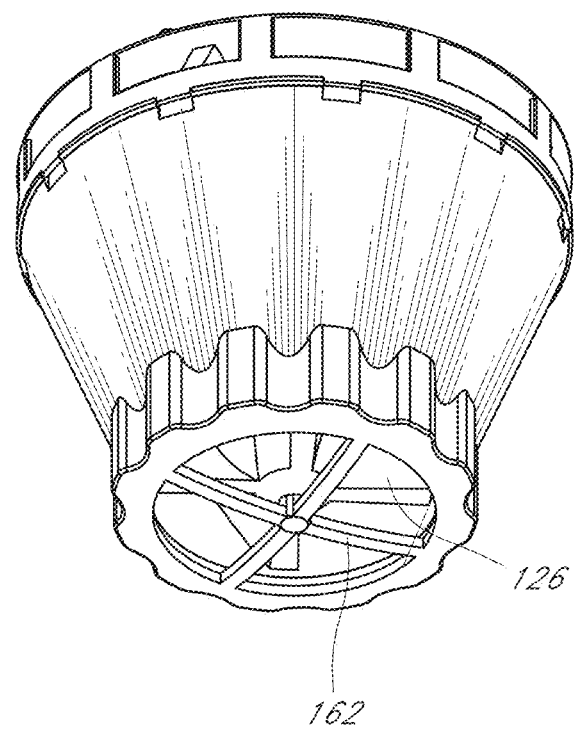
Figure 12C:
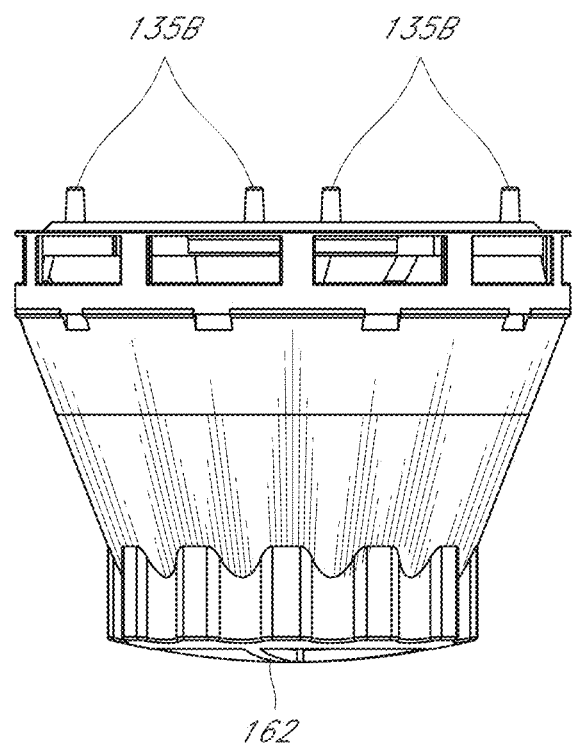
Figure 12D:
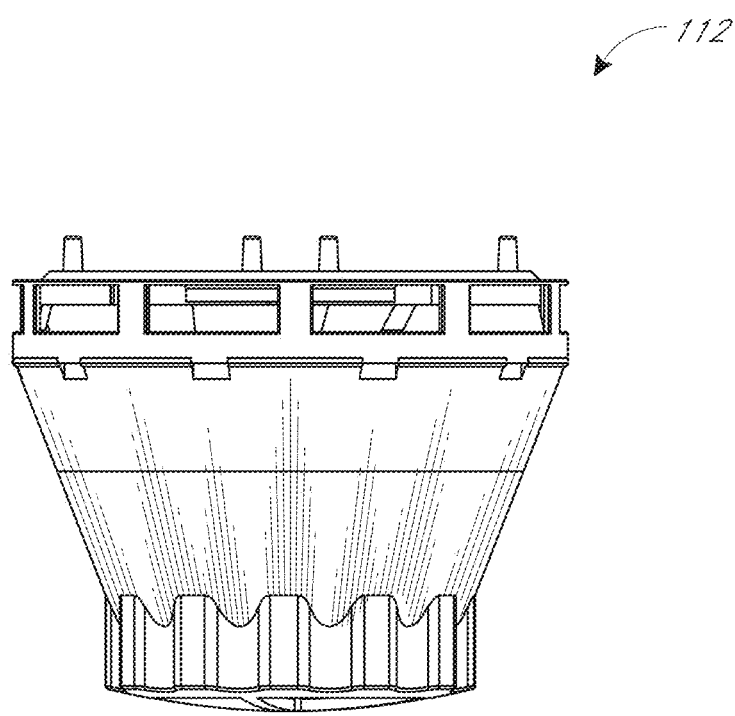
Figure 12E:
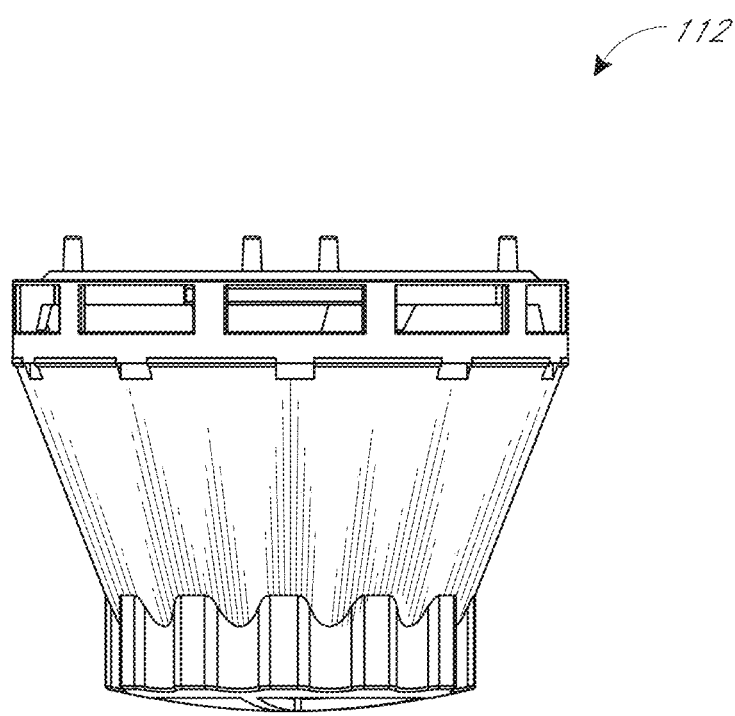
Figure 12F:
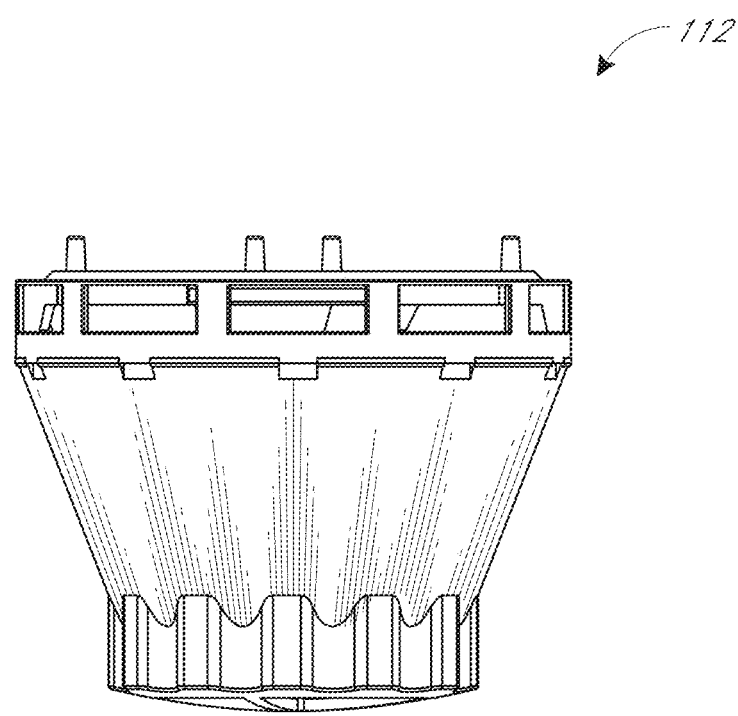
Figure 12G:
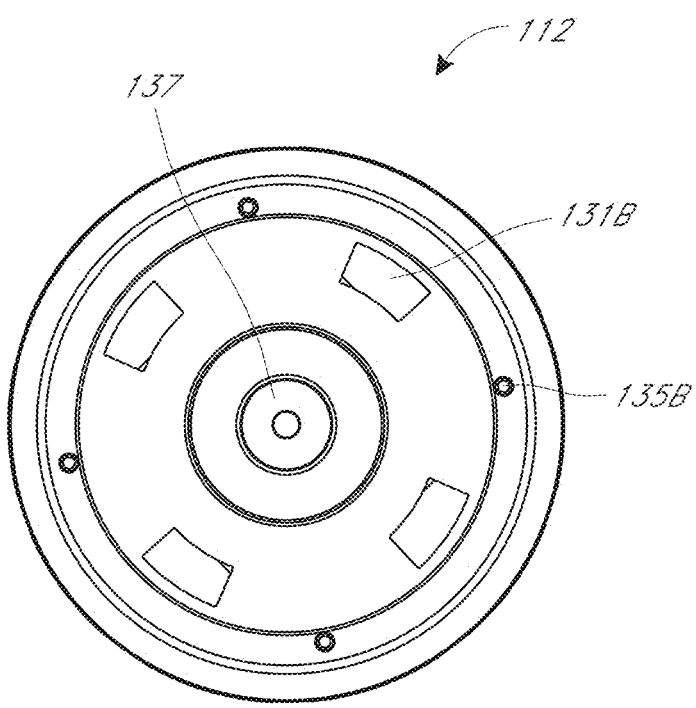
Figure 12H:
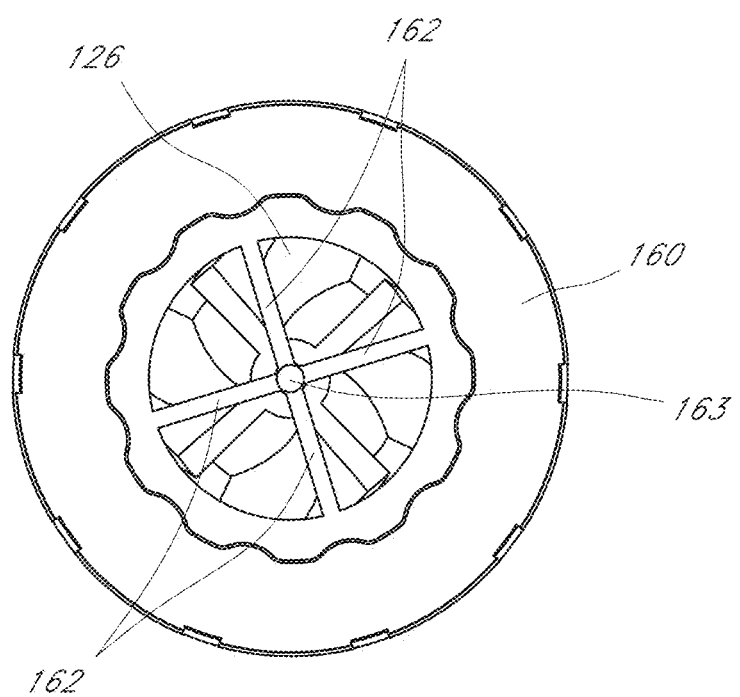

Because the second positioning features 135B of the cartridge 112 (e.g., the posts) are located in the holes 145 of the control gears 142, the movement of the control gears 142 cause movement of the posts too. For example, the posts 135B of the cartridge 112 can slide in the slots 135A of the support element 129. This causes the cartridge 112 to rotate relative to the support element 129 and/or to slide along the engagement element 130. As the cartridge 112 rotates, the securing features 131B (e.g., hooks) can rotate too, which can remove the physical interference holding the cartridge 112 in place. For example, the ends of the hooks can rotate back into the slots. Because the physical interference has been removed, the cartridge 112 is released and/or is no longer supported. The cartridge 112 can thus can be ejected from the support element 129 and/or can fall downward, such as by force of gravity. As is shown in FIG. 11, in the disengaged position, the cartridge 112 can be separated from the support element 129. The separation of the cartridge 112 from the support element 129 can occur because of and/or be furthered by the biasing members 134, which apply a downward force on cartridge 112 (e.g., via the engagement element 130). In certain embodiments, in the disengaged position, the cartridge 112 is spaced apart from the engagement element 130. In some variants, the cartridge 112 remains in contact with the engagement element 130 in the disengaged position.

The connection between the impeller 126 can the shaft 136 can detach during release of the cartridge 112. In some embodiments, the force of the biasing members 134 and/or the weight of the cartridge 112 can overcome the attractive force of the connecting elements 139A, 139B and/or the frictional force between the shaft 136 and walls of the cavity 137. Thus, as shown in the example of FIG. 11, the impeller 126 moves downward relative to (e.g., disengages at least partly from) the shaft 136 and/or the elements 139A, 139B separate from each other. In some embodiments, the impeller 126 can drop within the casing. For example, the impeller 126 can fall into contact with the stop 163. See FIG. 11.

In various embodiments, the cartridge 112 can fall to the disengaged position (see FIG. 5B). The cartridge 112 can be caught and/or inhibited from further downward movement by the catch 128. In some embodiments, the cartridge 112 drops at least about: 12 mm, 19 mm, 25 mm, or otherwise. The cartridge 112 can be maintained in the housing H even after the cartridge 112 has dropped. An observer can readily see the changed position of the cartridge 112 and recognize that replacement is needed.

III. Dispenser 210

Figure 13A:
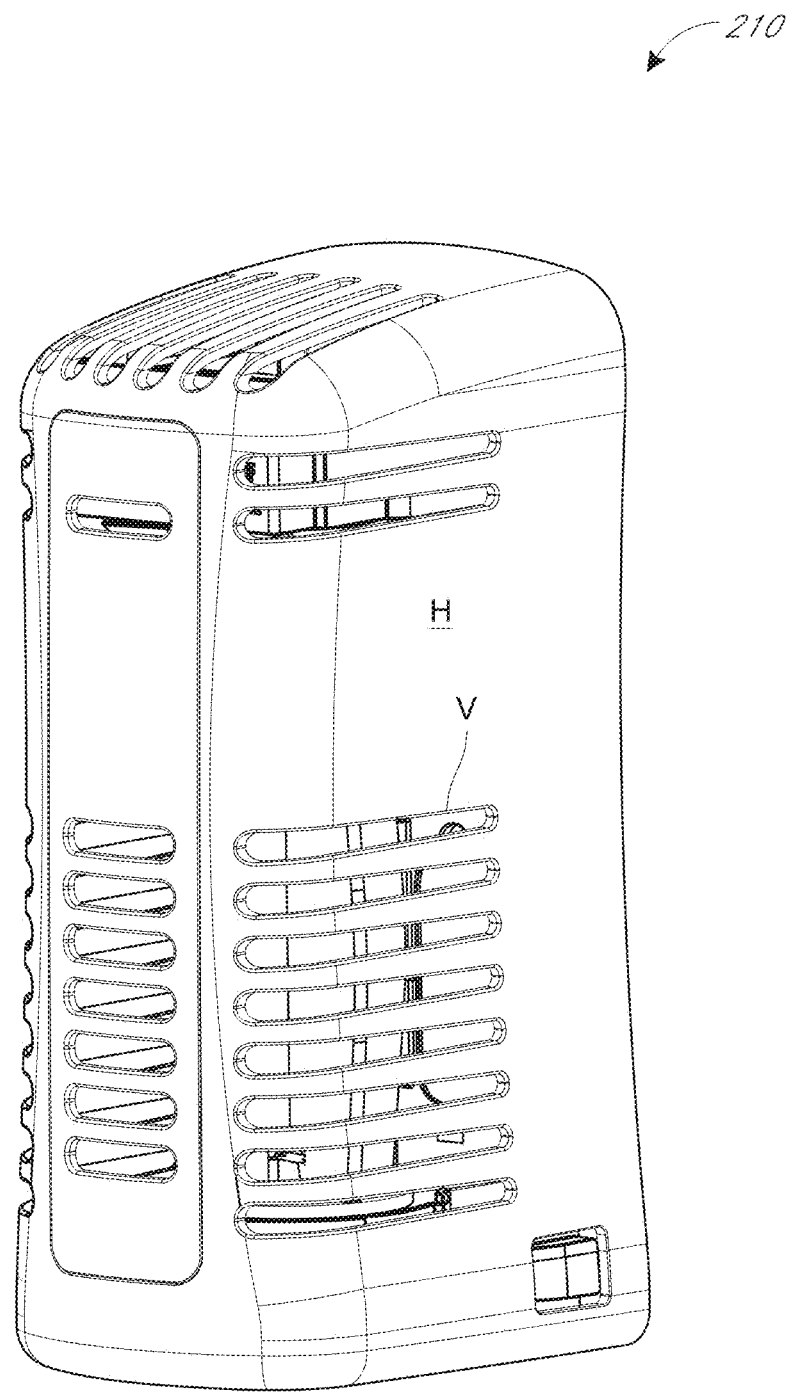
FIG. 13A illustrates another fragrance dispenser.
Figure 13B:
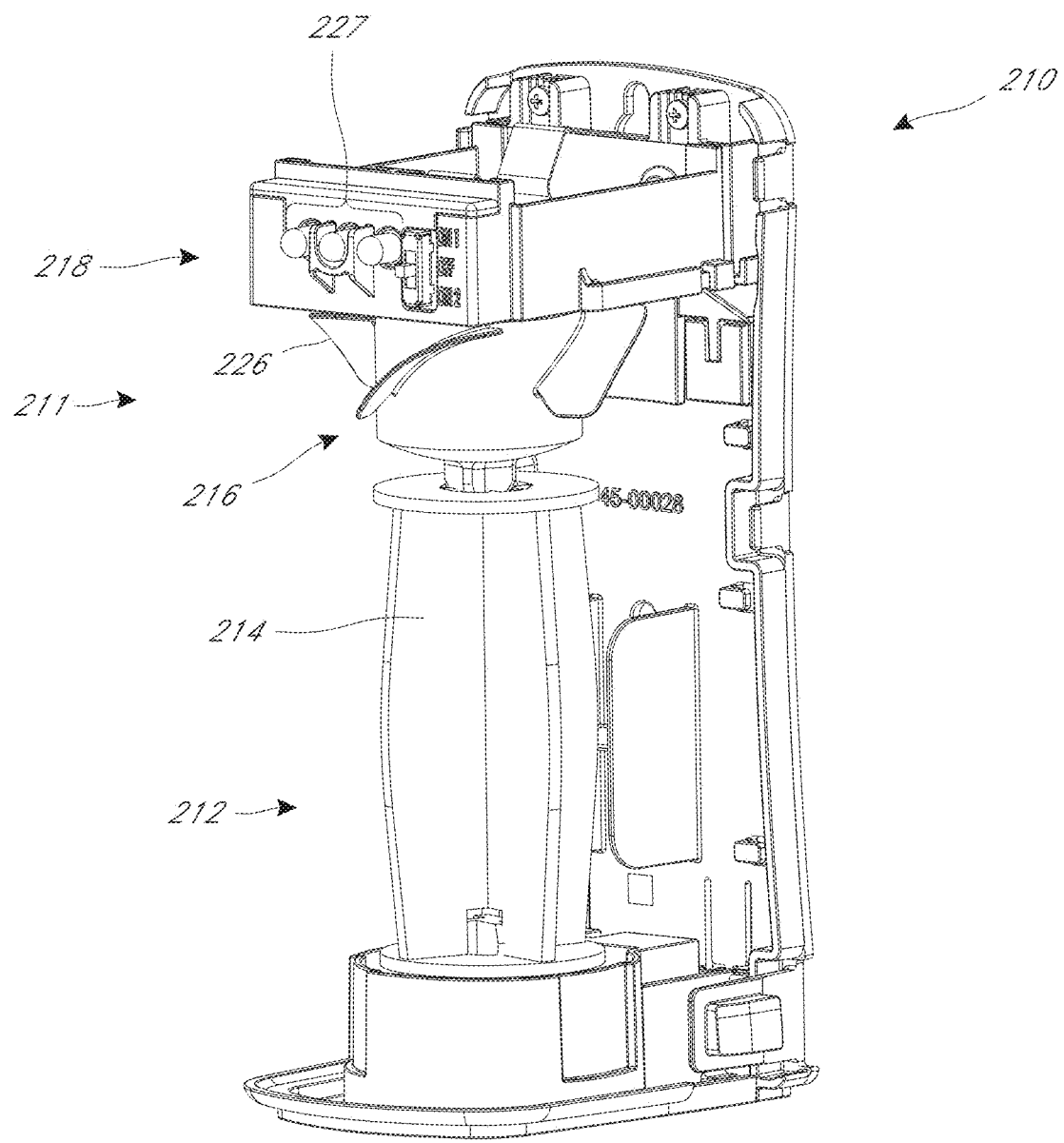
FIG. 13B illustrates the dispenser of FIG. 13A with a front housing removed.
Figure 13C:
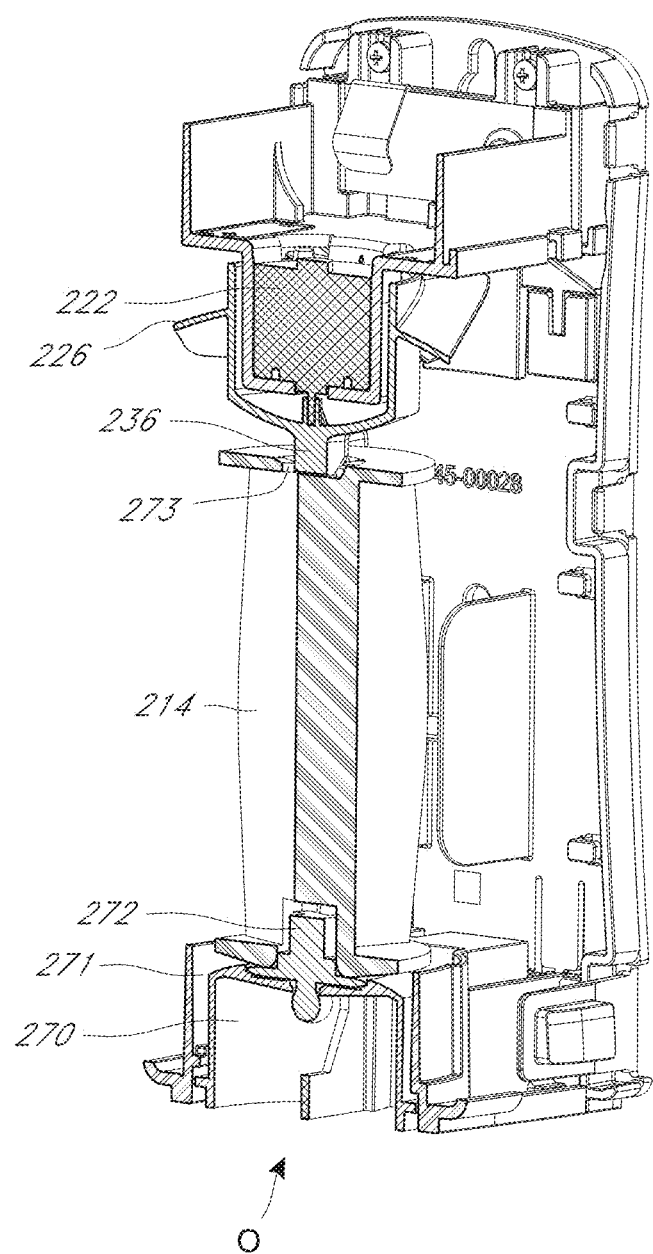
FIG. 13C illustrates a cross-sectional view of the dispenser of FIG. 13B.

FIGS. 13A-13C illustrate another embodiment of a dispenser 210. The dispenser 210 resembles and/or can include any of the features of the dispenser 10, 110. For example, as illustrated in FIG. 13A, the dispenser 210 can include a housing H with vents V. A front portion of the housing H can be removable, such as by sliding the front portion off a rear portion of the housing H.

As shown in FIGS. 13B and 13C, the dispenser 210 can include a core unit 211. The core unit 211 can include a connection unit 216 and a control unit 218. The connection unit 216 can include an impeller 226. Some embodiments do not include the impeller 226. The control unit 218 can include a controller and indicator unit, such as lights 227.

The dispenser 210 can include a cartridge 212. The cartridge 212 can be inserted into the housing H, such as through a lower opening O. In some embodiments, the cartridge 212 is inserted generally vertically and then rotated to secure it with a locking mechanism of the housing H, such as a bayonet connection mechanism. In certain variants, the cartridge 212 is rotated at least about: 45°, 60°, 90°, or more.

The cartridge 212 can include a fragrance reservoir 214. The fragrance reservoir 214 can include a plurality of fins. The cartridge 212 can include a base 270 (also called an adapter). The base 270 can be configured to mate in a corresponding recess 271 in the housing H. In some embodiments, the base 272 is fixedly attached to the housing H. The cartridge 212 can include a rotation element 272, such as a bearing or bushing. The rotation element 272 can enable the fragrance reservoir 214 to rotate relative to the base 270. The rotatable portion of the cartridge 212 can be a fan and/or may be combined with a fan. In some implementations, the rotatable portion of the cartridge 212 may be produced using a fragrance infused TPE.

The cartridge 212 can include a coupling region, such as a hub 273. In some embodiments, the hub 273 comprises a recessed portion. The hub 273 can be configured to mate with a corresponding coupling region of the connection unit 216, such as a shaft 236. The shaft 236 can be part of or mechanically connected to the motor 222. In some embodiments, the hub 273 is configured to receive rotational motion from the shaft 236. For example, an end of the shaft 236 can have one or more ribs or flutes that are received in corresponding grooves or notches in the hub 273, or vice versa. In some embodiments, the shaft 236 is part of and/or rigidly connected to the impeller 226.

The dispenser 210 can include a motor 222. In some embodiments, the motor 222 spins the shaft 236, which spins the fragrance reservoir 214. In certain implementations, the motor 222 spins the impeller 226. The motor 222 can comprise an electric motor. The motor 222 can be positioned above the cartridge 212.

The control unit 218 can be configured to control the motor 222, such as the rotational speed, "on time," and/or activation frequency. The controller can balance fragrance distribution over the life of the cartridge 212. In some embodiments, the controller activates the motor 222 such that the fragrance reservoir 214 rotates at a certain rotational speed, during an amount of time, stops for an amount of time and then repeats. In certain implementations, the amount of fragrance released is controlled by: the speed at which the fragrance reservoir 214 rotates, the length of time during which the fragrance reservoir 214 rotates, how often the fragrance reservoir 214 is activated (e.g., the time between intervals), and/or the type of fragrance reservoir 214. The time, speed, and intervals can be automatically adjusted as the fragrance in the fragrance is depleted, such as to maintain a similar (e.g., generally uniform) level of scent distribution. In some implementations, when new, the fragrance reservoir 214 will rotate slower, for less time, and/or will have longer intervals in between uses. In some implementations, nearing the end of life, the fragrance reservoir 214 will rotate faster, for longer period of time, and/or with shorter intervals in between uses.

IV. Dispenser 310

Figure 14A:
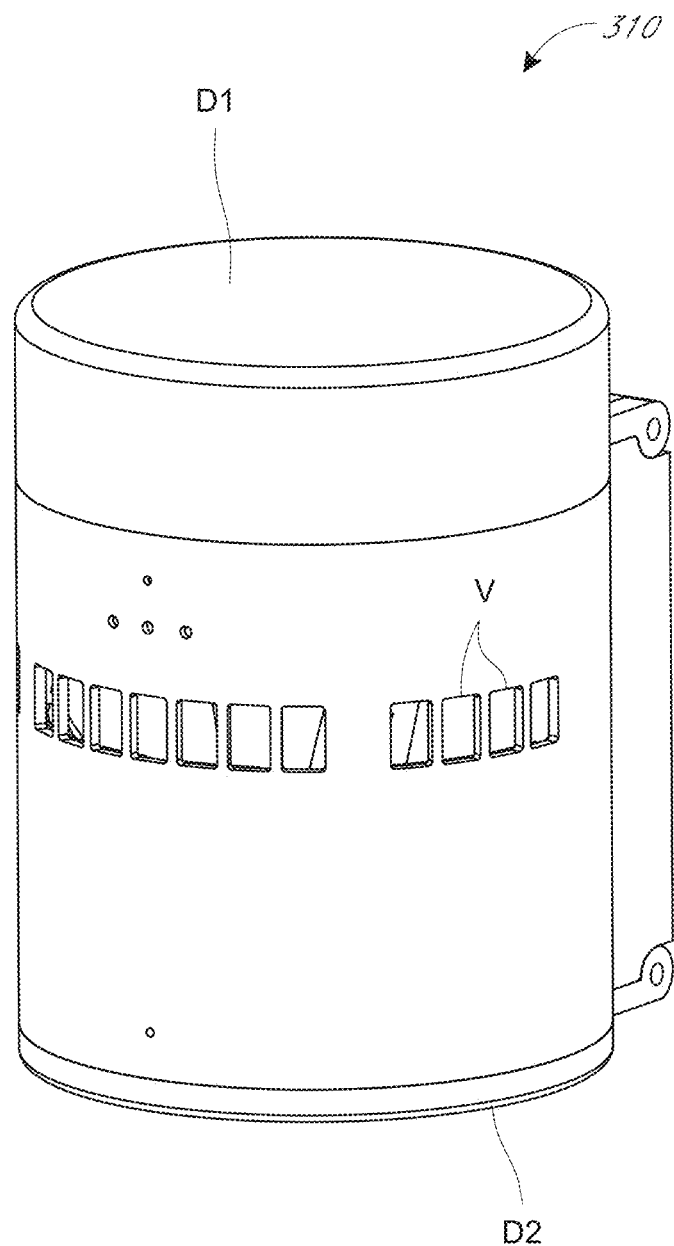
FIG. 14A illustrates another fragrance dispenser.
Figure 14B:
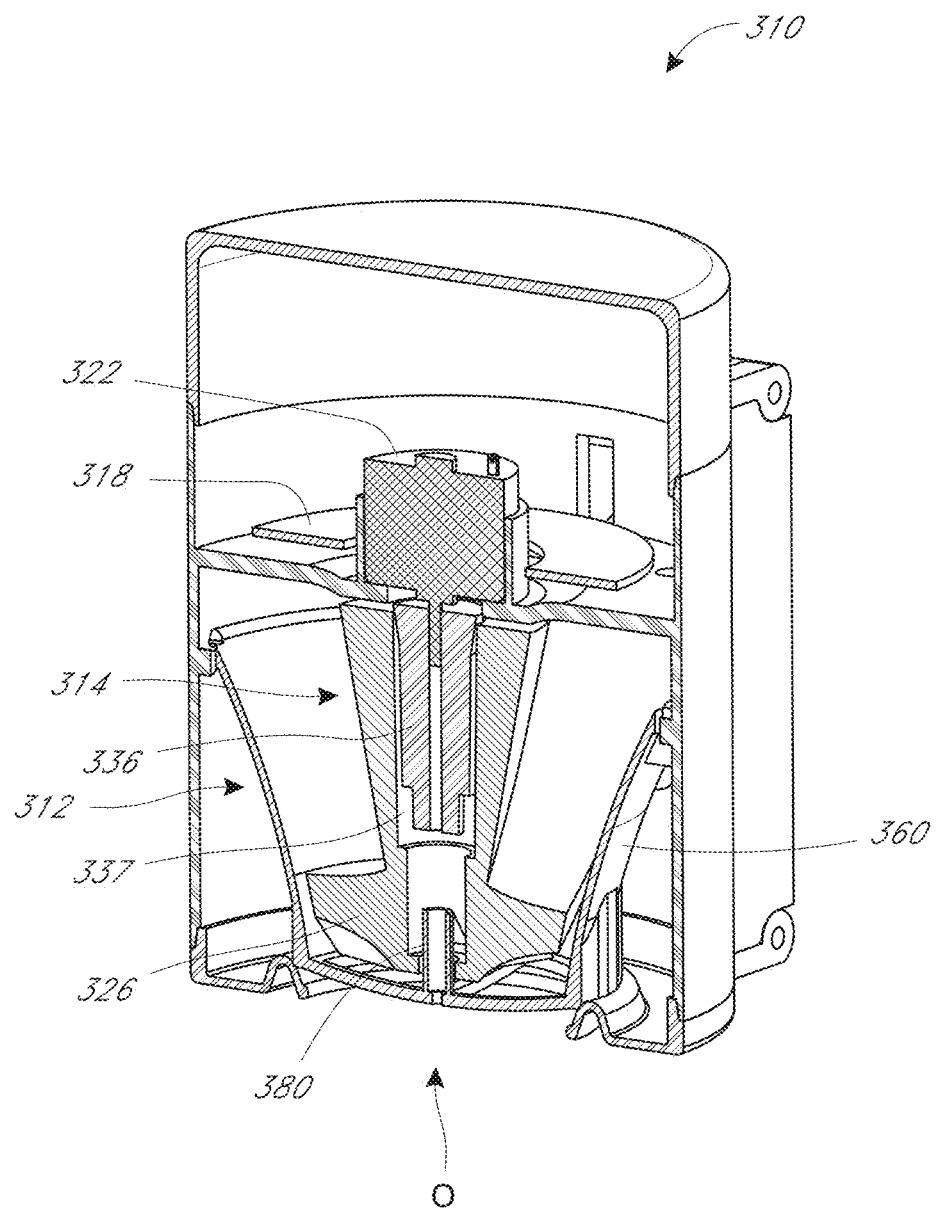
FIG. 14B illustrates a cross-sectional view of the dispenser of FIG. 14A.

FIGS. 14A and 14B illustrate another embodiment of a dispenser 310. The dispenser 310 resembles and/or can include any of the features of the dispenser 10, 110, 210. As illustrated, the dispenser 210 can include a housing H with vents V, a first door D1, and a second door D2. The first door D1 can be on a top of the dispenser 310. The first door D1 can provide access to portions of a core unit 311, such as a controller 318 (e.g., PCB), motor 322, and/or power supply. In some embodiments, the power supply comprises batteries. The second door D2 can be on a bottom of the dispenser 310. The second door D2 can provide access to a cartridge 312. For example, a user can open the second door D2 to install or remove the cartridge 312. Air can access the cartridge 312 through the vents V and a bottom opening O.

The cartridge 312 can include a fragrance reservoir 314 in an outer casing, such as a shell 160. In some implementations, the fragrance reservoir 314 is enclosed in the cartridge 312. In some variants, the cartridge 312 is open, such as on the top, and/or does not include a lid. The fragrance reservoir 314 can comprise an impeller 326, such fan blades. In some embodiments, the impeller 326 is rotatable about a central axle 380, such as a post projecting upward from a bottom of the cartridge 312. The impeller 326 can have a cavity 337 that is configured to receive a shaft 336 of the core unit 311. The shaft 336 can be rotatable by the motor 322. In some embodiments, the motor 322 is a direct drive motor. The cavity 337 and shaft 336 can couple such that rotational motion can be transferred from the shaft 336 to the impeller 326. For example, in some implementations, the shaft 336 is received in the cavity 337 with an interference fit, such as an interference in a radial direction. In some variants, the shaft 336 and impeller 326 are connected with attractive magnetic elements, such as a magnet on an end of the shaft 336 and a metal element (e.g., a washer) in the cavity 337. The motor 322 can drive the shaft 336 to drive the impeller 326, thereby dispensing fragrance.

V. Certain Terminology

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees and the term "generally perpendicular" can refer to something that departs from exactly perpendicular by less than or equal to 20 degrees.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

VI. Summary

The technology of the present disclosure has been discussed in the context of certain embodiments and examples.

The technology extends beyond the specifically disclosed embodiments to other alternative embodiments and/or uses of the embodiments and certain modifications and equivalents thereof. For example, although certain embodiments are disclosed in the context of a dispenser with a fan, the technology can be applied to dispensers without fans too. As another example, while some embodiments have been described in which the cartridge is replaced, in some variants the cartridge is configured for reuse, such as having a refillable fragrance reservoir. The fragrance dispensers can include any feature from any of U.S. Pat. Nos. 8,573,447, 8,860,347, 8,889,082, and 8,931,713, which are incorporated by reference herein in their entirety, but shall not be used for construing the claims herein. Any two or more of the components of the dispenser system can be made from a single monolithic piece or from separate pieces connected together. Various features and aspects of the disclosed embodiments can be combined with or substituted for one another in order to form varying modes of the invention. The scope of this disclosure should not be limited by the particular disclosed embodiments described herein.

Certain features that are described in this disclosure in the context of separate implementations can also be implemented in combination in a single implementation. Conversely, various features that are described in the context of a single implementation can also be implemented in multiple implementations separately or in any suitable subcombination. Although features may be described above as acting in certain combinations, one or more features from a claimed combination can, in some cases, be excised from the combination, and the combination may be claimed as any subcombination or variation of any subcombination.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying drawings. The figures are drawn to scale, but such scale is not limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

In summary, various embodiments and examples of fragrance dispensers and related processes have been disclosed. Although the dispensers and processes have been disclosed in the context of those embodiments and examples, the technology of this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described above, but should be determined only by a fair reading of the claims that follow.

The following is claimed:

1. A fragrance dispenser system comprising:
 a housing;
 a core unit in the housing, the core unit comprising:
  a connection unit comprising:
   a securing element comprising a plurality of first securing features;
   an engagement element comprising an annular member that is configured to move relative to the securing element; and
   a biasing member that biases the engagement element away from the securing element;
  a control unit comprising a controller and a cartridge sensor; and
  an electric motor comprising a drive shaft, the drive shaft configured to spin in a first rotational direction and a second rotational direction;
 a cartridge configured to removably engage with the core unit, the cartridge comprising:
  a plurality of second securing features, the second securing features configured to mate with the first securing features;
  an impeller; and
  a fragrant material;
 the fragrance dispenser system configured such that:
  when the cartridge is engaged with the core unit and the drive shaft spins in the first rotational direction, the impeller spins; and
  when the drive shaft spins in the second rotational direction, the cartridge disengages from the connection unit.

2. The system of claim 1, further comprising a plurality of first positioning features and a plurality of second positioning features that are configured to engage with the plurality of first positioning features.

3. The system of claim 2, wherein the first positioning features comprise slots and the second positioning features comprise posts.

4. The system of claim 1, wherein the first securing features comprise hooks and the second securing features comprise openings.

5. The system of claim 2, wherein the connection unit further comprises a control gear that is movable by the motor and that is configured to engage with at least one of the second positioning features.

6. The system of claim 1, the connection unit further comprises a one-way torque transmission device configured to activate to transmit torque only when the drive shaft spins in the second rotational direction.

7. The system of claim 1, wherein the cartridge sensor is configured to detect that the cartridge is secured to the connection unit.

8. The system of claim 1, wherein, when the cartridge disengages from the connection unit, a bottom of the cartridge protrudes out of the housing.

9. A fragrance dispenser system comprising:
a housing with a catch;
a core unit comprising:
  a connection unit;
  a control unit; and
  a motor;
a cartridge configured to removably engage with the core unit, the cartridge comprising:
  an impeller; and
  a fragrant material;
the fragrance dispenser system configured such that:
  when the cartridge is engaged with the core unit, the impeller is rotatable by the motor; and
  when the cartridge reaches a depleted state, the cartridge is disengaged from the connection unit and drops from an engaged position to a disengaged position,
wherein the catch holds the cartridge in the disengaged position.

10. The system of claim 9, further comprising:
a cartridge present sensor configured to detect that the cartridge is engaged with the connection unit; and
a cartridge secured sensor configured to detect that the cartridge is secured to the connection unit.

11. The system of claim 9, wherein the impeller comprises a lattice of thermoplastic elastomer.

12. The system of claim 9, wherein the catch comprises an arm or a flange.

13. The system of claim 9, wherein the connection unit comprises:
a support element that is configured to removably secure with the cartridge; and
an engagement element that is configured to move vertically relative to the support element and is biased away from the support element by a biasing member.

14. The system of claim 9, wherein the connection unit further comprises a shaft that is configured to be received in a cavity of the impeller.

15. The system of claim 14, wherein the shaft comprises a magnet, and wherein when the cartridge is engaged with the core unit the impeller is suspended above a stop on a bottom of the cartridge by the force of the magnet.

16. The system of claim 14, wherein the shaft comprises a plurality of radially outwardly extending wings.

17. A method of operating a fragrance dispenser, the method comprising:
receiving a fragrance cartridge into a housing of the fragrance dispenser;
rotating the cartridge relative to a support element of the fragrance dispenser, thereby engaging first and second securing features of the support element and cartridge, respectively;
operably connecting a motor of the fragrance dispenser with an impeller of the fragrance cartridge;
driving the motor in a first rotational direction, thereby spinning the impeller;
driving the motor in a second rotational direction, thereby engaging a one-way torque transmission device;
transmitting torque from the motor and via the one-way torque transmission device to the cartridge, thereby rotating the cartridge relative to the support element;
disengaging the first and second securing features; and
dropping the fragrance cartridge into a disengaged position.

18. The method of claim 17, wherein dropping the fragrance cartridge comprises pushing the fragrance cartridge away from the support element with a biasing member.

19. The method of claim 17, wherein operably connecting the motor of the fragrance dispenser with the impeller of the fragrance cartridge comprises receiving a shaft of the support element into a cavity of the impeller.

20. The method of claim 17, wherein engaging the first and second securing features comprises rotating a hook of the support element relative to an opening in the cartridge.

21. The method of claim 17, further comprising determining, with an electronic controller of the fragrance dispenser, that the cartridge has reached a depleted state.

22. A fragrance dispenser system comprising:
a core unit comprising:
  a connection unit;
  a control unit; and
  a motor;
a cartridge configured to removably engage with the core unit, the cartridge comprising:
  an outer casing;
  an impeller that is movable within the outer casing, the impeller configured to rotate around an axis of rotation and to slide along the axis of rotation; and
  a fragrant material;
the fragrance dispenser system configured such that, as the cartridge is engaged with the core unit, the impeller slides upward relative to the outer casing.

23. The system of claim 22, wherein the connection unit comprises a first magnetic element and the impeller comprises a second magnetic element, the first and second magnetic elements being attracted by magnetic force.

24. The system of claim 22, wherein the fragrance dispenser system is further configured such that, while the cartridge is engaged with the core unit, the impeller is suspended above and spaced apart from a stop on the outer casing.

25. A fragrance dispenser system comprising:
a core unit comprising:
  a connection unit having a shaft with a magnet;
  a control unit; and
  a motor; and
a cartridge configured to removably engage with the core unit, the cartridge comprising:
  an impeller comprising a cavity configured to receive the shaft; and
  a fragrant material;
the fragrance dispenser system configured such that:
  when the cartridge is engaged with the core unit, the impeller is rotatable by the motor and is suspended above a stop on a bottom of the cartridge by the force of the magnet; and
  when the cartridge reaches a depleted state, the cartridge is disengaged from the connection unit and drops from an engaged position to a disengaged position.

* * * * *